United States Patent [19]

Urban et al.

[11] Patent Number: 5,626,597
[45] Date of Patent: May 6, 1997

[54] PERCUTANEOUS INTRODUCER

[75] Inventors: Carl T. Urban, Portland, Oreg.; Scott W. Larsen, Newtown; Marc J. Theroux, Bethel, both of Conn.

[73] Assignee: United States Surgical Corporation, Norwalk, Conn.

[21] Appl. No.: 391,882

[22] Filed: Feb. 21, 1995

[51] Int. Cl.$^6$ ............................................ A61B 17/32
[52] U.S. Cl. .................... 606/170; 606/159; 606/205
[58] Field of Search .................... 606/128, 170, 606/176, 184, 185, 186, 205, 206, 207, 167; 604/33, 156, 164, 167

[56]           References Cited

U.S. PATENT DOCUMENTS

| | | |
|---|---|---|
| 2,898,917 | 8/1959 | Wallace . |
| 3,487,837 | 1/1970 | Petersen . |
| 4,170,995 | 10/1979 | Levine et al. . |
| 4,535,773 | 8/1985 | Yoon . |
| 4,556,059 | 12/1985 | Adamson, Jr. . |
| 4,601,710 | 7/1986 | Moll . |
| 4,915,694 | 4/1990 | Yamamoto et al. . |
| 5,073,169 | 12/1991 | Raiken . |
| 5,152,754 | 10/1992 | Plyley et al. . |
| 5,224,930 | 7/1993 | Spaeth et al. ............................ 606/167 |
| 5,352,235 | 10/1994 | Koros et al. ............................ 606/170 |
| 5,383,888 | 1/1995 | Zvenyatsky et al. .................... 606/170 |

FOREIGN PATENT DOCUMENTS 0595479  5/1994  European Pat. Off. .

*Primary Examiner*—Michael Buiz
*Assistant Examiner*—Kevin Truong

[57]           ABSTRACT

A surgical instrument for percutaneous accessing body tissue including a tissue piercing element for creating an opening through a body wall. The surgical instrument may include a working member for performing a surgical procedure within the body. Alternatively, the surgical instrument may include an introducer having a stabilizing structure for facilitating the passage of the tissue piercing element and for releasably affixing the surgical instrument to the body tissue surface, thereby securing the surgical instrument relative to the patient's body.

44 Claims, 17 Drawing Sheets

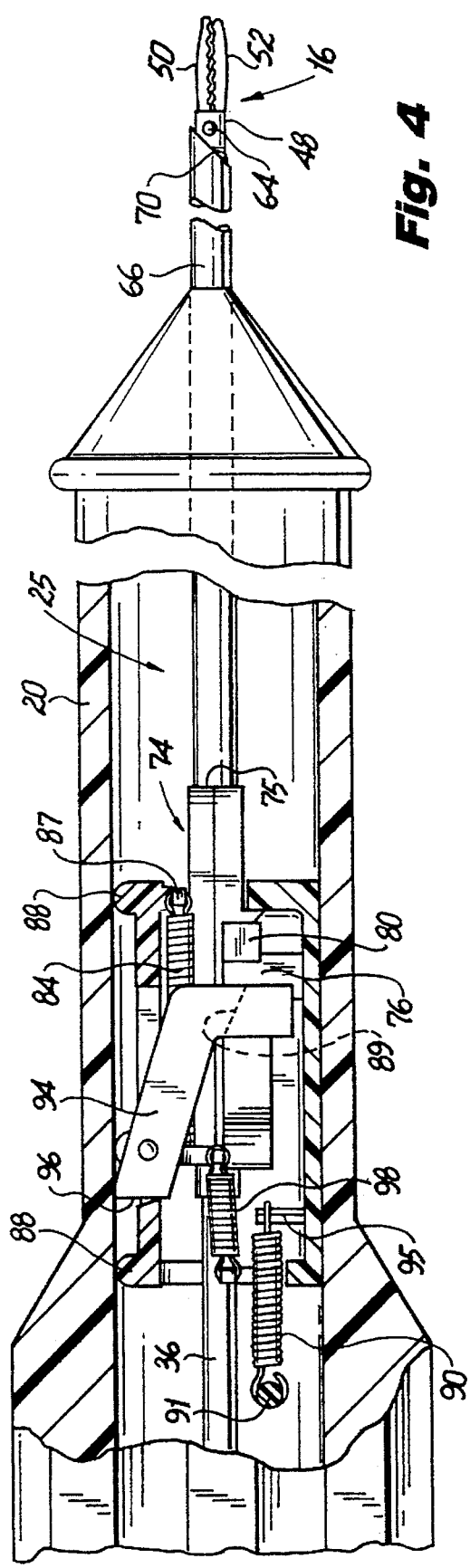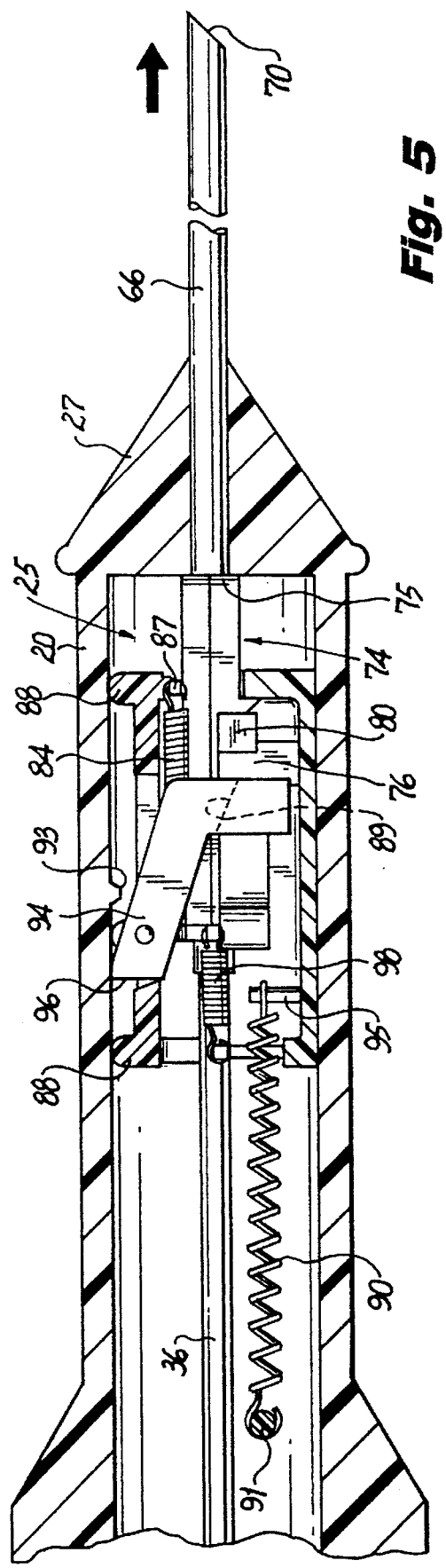
Fig. 4
Fig. 5

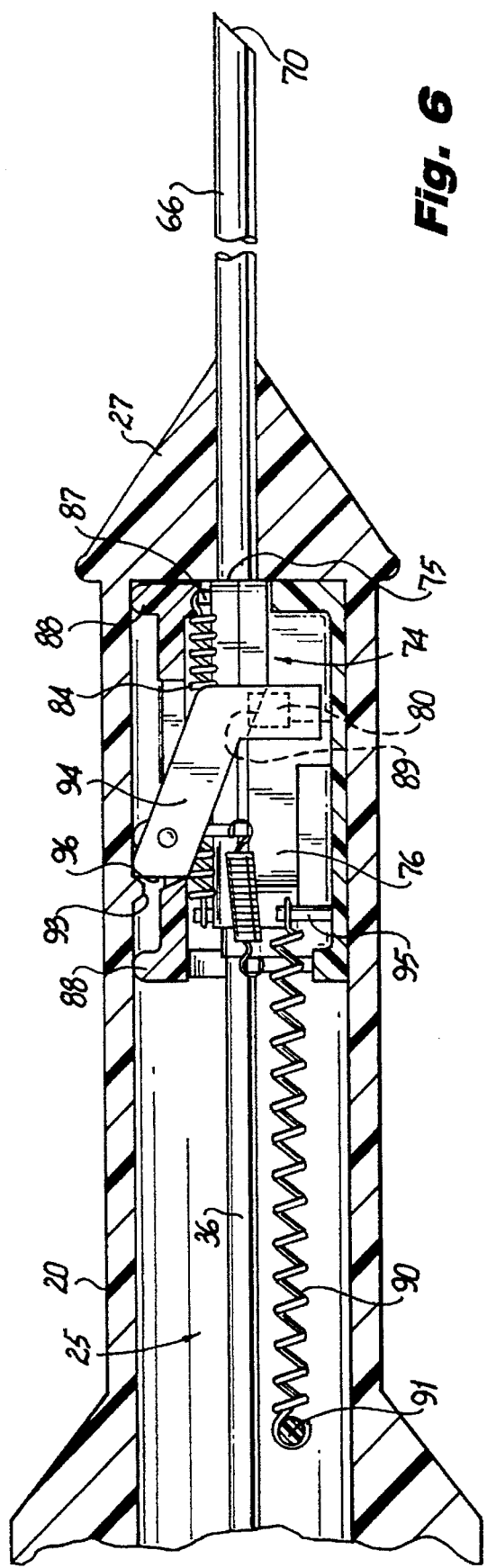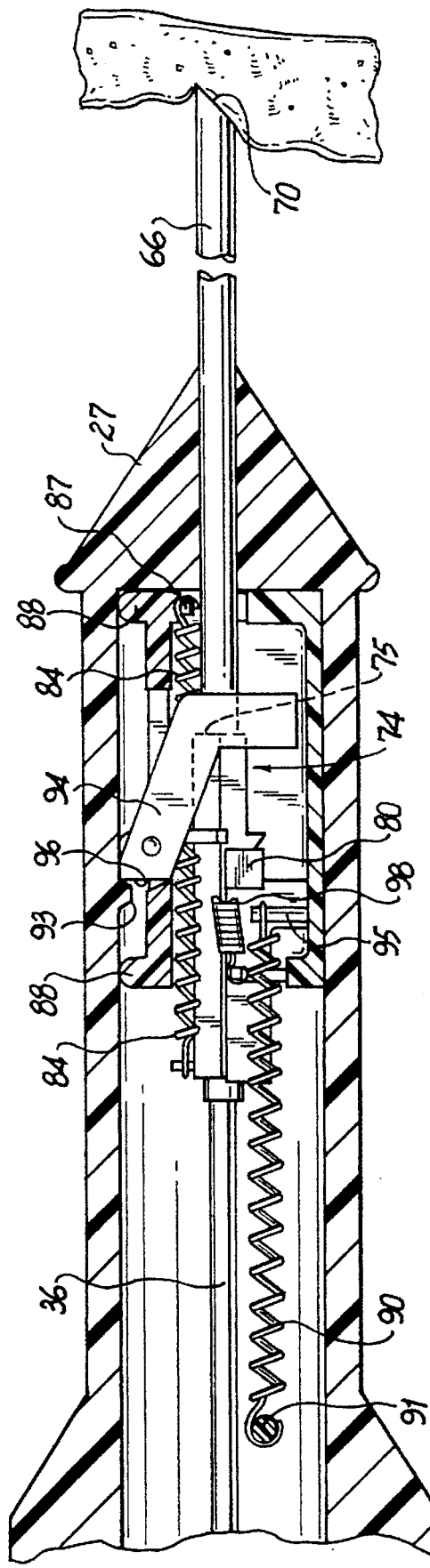

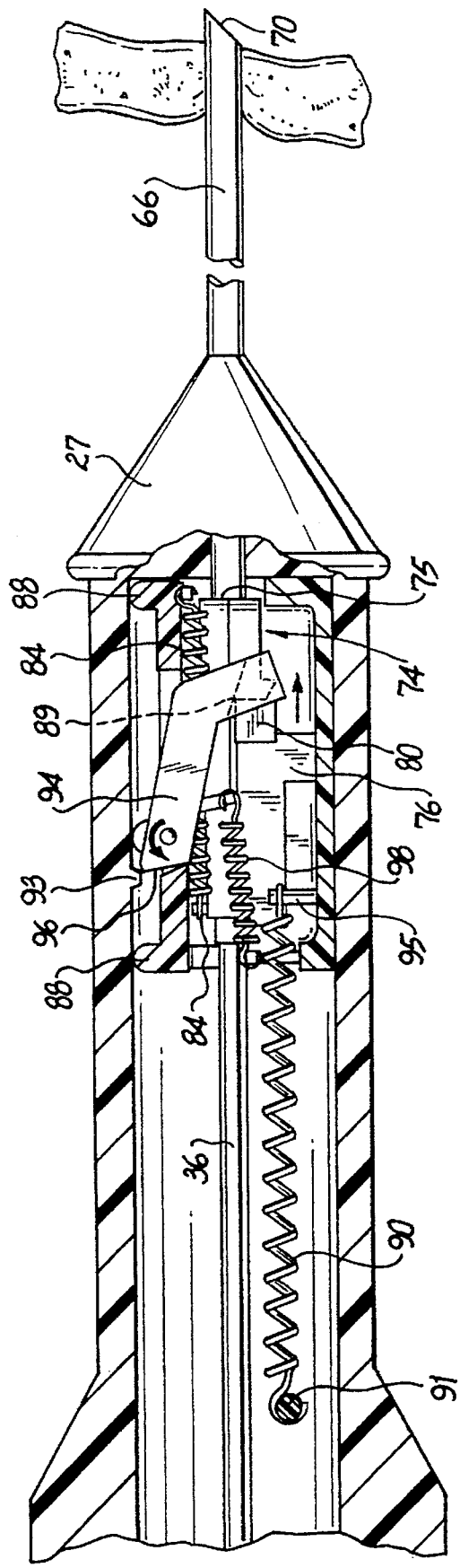

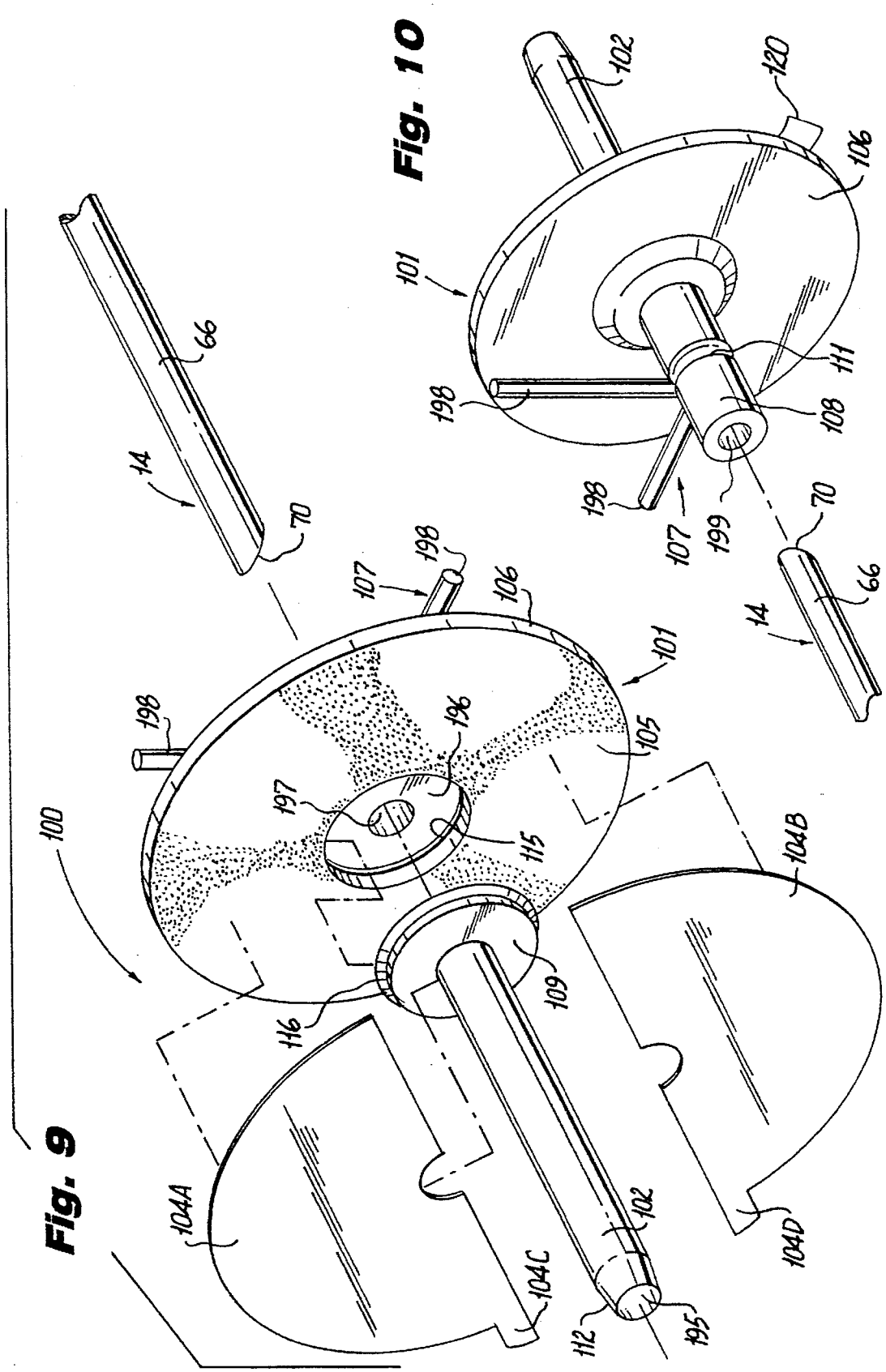

PERCUTANEOUS INTRODUCER

BACKGROUND

1. Technical Field

This disclosure relates to a surgical instrument and, more particularly, to a surgical instrument for percutaneously accessing an operative site within a body.

2. Background of Related Art

Accessing body tissue within a body cavity or beneath the skin involves creating an opening in the skin through which different types of surgical instruments are inserted to perform various surgical or diagnostic functions. The opening of the skin to access an operative site is usually created by incising with a surgical knife or by puncturing through the skin with an instrument having a sharp tip such as a needle or an obturator. Additional instruments are then inserted through the incision to perform the surgical procedure. For example, the surgeon may use one instrument for piercing the skin to introduce a pressurized gas to inflate or distend the surgical site, an endoscope for viewing areas or objects surrounding the surgical site and other instruments for performing surgical functions such as shearing and stapling. Therefore, frequent insertions and withdrawals of surgical instruments through the skin opening are typical. These insertions and withdrawals through the skin opening may traumatize the body tissue surface layer which surrounds the skin opening, enlarge the incision or opening, and/or create room for undesired or inadvertent movement of the surgical instrument during the surgical procedure.

A trocar is one commonly used surgical instrument for creating a port of entry through the skin. A trocar guide sleeve is thus positioned for receiving surgical instruments and for facilitating passage of the surgical instruments through the skin opening. However, unless the trocar guide sleeve is somehow affixed in a stationary position with respect to the body, the frequent insertion and withdrawal of surgical instruments may move the sleeve, causing enlargement of the incision and/or trauma to the surrounding tissues. Moreover, whether or not a sleeve is fixed or held stationary relative to the body, manipulative movement of the surgical instrument while it is received in the sleeve may be inhibited.

A variety of percutaneous instruments for providing communication through the surface of body tissue are known. Known percutaneous instruments typically include a cutting or puncturing implement and some sort of safety mechanism, e.g., a spring-biased blunt styler or shielding tube which is biased to protrude beyond the distal end of the cutting implement to obstruct anatomical organs from making cutting contact with the cutting implement. Examples of devices which include spring-biased safety mechanisms and provide for percutaneous introduction include conventional Verres needles and the devices shown in U.S. Pat. No. 4,535,773 to Yoon; U.S. Pat. No. 4,556,059 to Adamson, Jr.; U.S. Pat. No. 4,601,710 to Moll; and U.S. Pat. No. 5,152,754 to Plyley et al.

Various trocars and devices for securing other surgical devices relative to a patient's body have also been proposed. See for example, U.S. Pat. No. 2,898,917 to Wallace, U.S. Pat. No. 3,487,837 to Petersen, U.S. Pat. No. 4,170,995 to Levine et al. and U.S. Pat. No. 4,915,694 to Yamamoto et al. Devices for supporting surgical instruments larger than catheters have also been proposed. For example, U.S. Pat. No. 5,073,169 to Raiken discloses a trocar support having an elastic membrane having an aperture to receive the trocar. The elastic membrane has a flat base for adhering to the patient's skin.

Notwithstanding the devices discussed above, a need remains for an instrument which minimizes the passage of surgical instruments through the skin opening, thereby minimizing potential enlargement of and trauma to the incision site. The surgical instrument disclosed herein provides such advantageous features.

SUMMARY

A surgical instrument is provided for percutaneously accessing an operative site within a body and for performing a surgical procedure within the body. The surgical instrument includes a frame having first and second ends, and a tissue piercing assembly having an elongated tubular portion forming a tissue piercing portion at a distal end. The elongated tubular portion defines a longitudinal axis. A tool assembly is disposed at least partially within the elongated tubular portion and has at least one working member. The surgical instrument further includes an actuating mechanism operatively associated with the frame and the tool assembly. The actuating mechanism manipulates the at least one working member in connection with the surgical procedure.

In another embodiment, the surgical instrument includes a control assembly disposed adjacent the second end of the frame and operatively associated with the tissue piercing assembly. The control assembly controls longitudinal movement of the tissue piercing assembly and is configured to move the elongated tubular portion between a first position wherein the at least one working member is recessed within the elongated tubular portion and a second position wherein the at least one working member extends distally out from the distal end of the tissue piercing assembly. When in the first position, the tubular portion prevents manipulation of the at least one working member. The control assembly includes structure which maintains the elongated tubular portion in the second position. When in the second position, an operator may engage skin with the tissue piercing portion of the elongated tubular portion.

The control assembly automatically retracts the elongated tubular portion to a retracted position proximal that of the at least one working member upon piercing of the skin by the tissue piercing portion. The actuating mechanism includes a movable handle pivotally connected at a first end to the frame, and at least one linking member having a first end operatively associated with the tool assembly and a second end operatively associated with the first end of the movable handle. Movement of the movable handle moves the at least one linking member to manipulate the at least one working member.

In another embodiment of the surgical instrument, a novel introducer is included for accessing an interior portion of a patient's body. The introducer is adapted to be affixed relative to the access opening and facilitates the passage of at least a portion of the tissue piercing assembly therethrough. The introducer, however, is not limited to use only with the surgical instrument embodiments described herein; rather, it is envisioned that one skilled in the art could find use of the introducer with other surgical instruments. Optionally, one portion of the introducer may function as a trocar. That portion is inserted and disposed in the opening for guiding a surgical instrument. Another portion of the introducer is affixed to the body tissue surface thereby securing the inserted surgical instrument relative to the body of a patient.

Briefly, the introducer includes: a stabilizing structure defining a longitudinal axis and having a longitudinally extending bore therethrough for receiving a surgical instrument, a flexible tissue anchoring skirt positioned adjacent a distal end portion of the stabilizing structure, the skirt having an opening therein in communication with and concentric to the longitudinal bore of the stabilizing structure and a tissue engaging surface for releasably affixing the introducer to a body tissue surface; and an accessing element extending distally from the flexible tissue anchoring skirt, the accessing element having a longitudinal bore therethrough, the longitudinal bore of the accessing element being in concentric alignment and communication with the skirt opening and the stabilizing structure bore. The accessing element typically has a distally tapering distal end portion for accessing body tissue.

The tissue piercing assembly is adapted for insertion through the stabilizing structure to puncture body tissue. Alternatively, prior to insertion of the tissue piercing assembly, an obturator having a sharp tip may be inserted through the stabilizing structure and the accessing element to initially puncture the body tissue and thereby facilitate insertion of the tissue piercing assembly.

Another embodiment of the introducer includes stabilizing structure having a collar defining a longitudinal axis and having a longitudinally extending bore therethrough for receiving a surgical instrument, a flexible tissue anchoring skirt positioned adjacent a distal end portion of the stabilizing structure, the skirt having an opening therein in communication with and concentric to the longitudinal bore of the collar and a tissue engaging surface for releasably affixing the surgical instrument to a body tissue surface; and an accessing element extending distally from the flexible tissue anchoring skirt, the accessing element having a longitudinal bore therethrough, the longitudinal bore of the accessing element being in concentric alignment and communication with the skirt opening and the collar bore. The accessing element typically has a distally tapering stub having a distal end tip for accessing body tissue. Advantageously, the introducer described hereinabove eliminates the need for a separate obturator for creating an opening in the body tissue.

BRIEF DESCRIPTION OF THE DRAWINGS

Various embodiments are described hereinbelow with reference to the drawings, wherein:

FIG. 4 is a side elevational cut-away view of the control assembly of FIG. 3 illustrating the control assembly at the rest position;

FIG. 5 is a view similar to that of FIG. 4 illustrating the control assembly at an advanced position;

FIG. 6 is a view similar to that of FIG. 5 illustrating the control assembly with the catch secured and the cutting tip covered;

FIG. 7 is a view similar to that of FIG. 6 illustrating the control assembly with the cutting tip contacting tissue;

FIG. 8 is a view similar to that of FIG. 7 illustrating the control assembly with the catch partially rotated out of the catch notch and the cutting tube in the retraction stroke;

FIG. 9 is a distal to proximal perspective view of an introducer constructed in accordance with another preferred embodiment;

FIG. 10 is a proximal to distal perspective view of the introducer of FIG. 9;

DETAILED DESCRIPTION OF PREFERRED EMBODIMENTS

Figure 1:
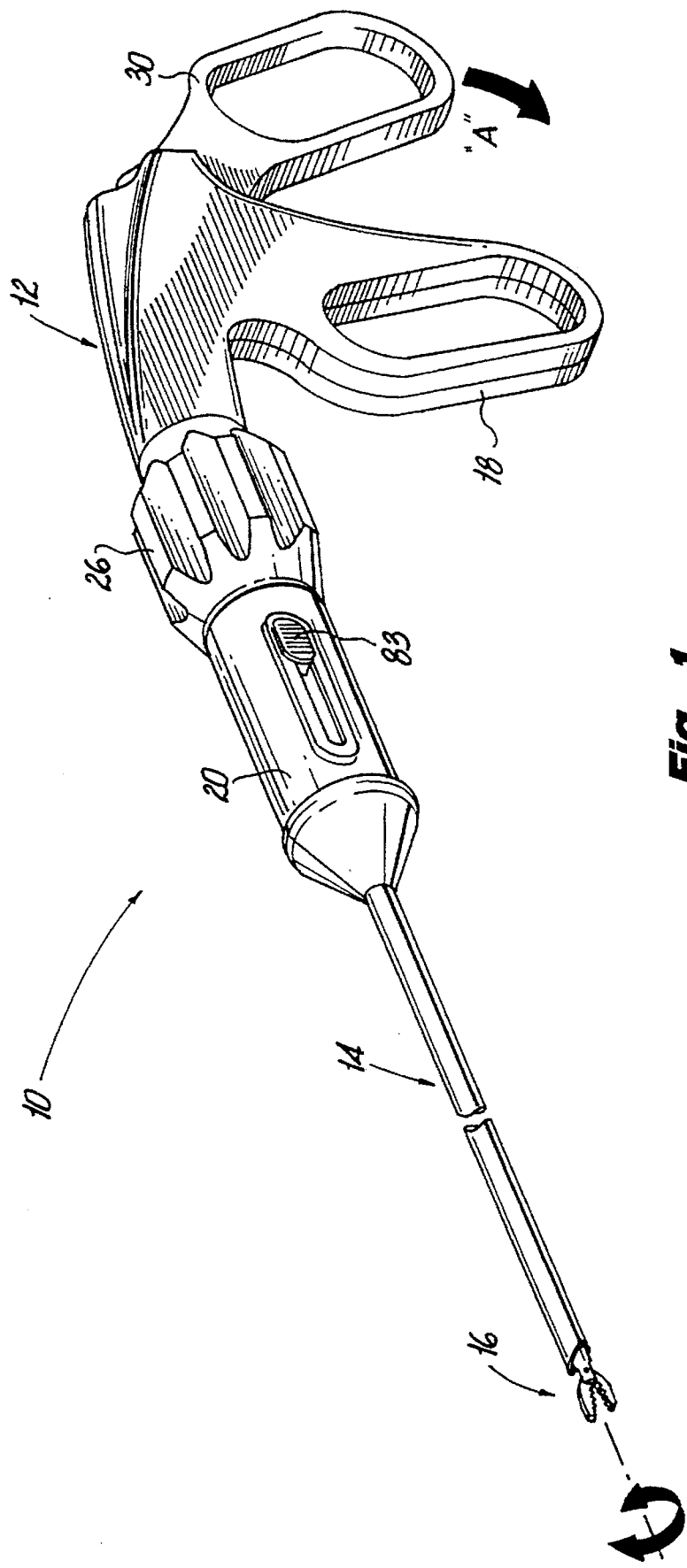
FIG. 1 is a perspective view of a surgical instrument constructed in accordance with a preferred embodiment.

In the drawings and in the description which follows, the term "proximal", as is traditional, will refer to the end of the surgical instrument which is closest to the operator, while the term "distal" will refer to the end which is furthest from the operator.

Referring now to the drawings wherein like reference numerals indicate similar structural elements of the subject disclosure, there is illustrated in FIG. 1 an exemplary surgical instrument designated generally by reference numeral 10. Surgical instrument 10 includes three main structural portions, namely frame 12, tissue piercing assembly 14, and tool assembly 16.

Figure 2:
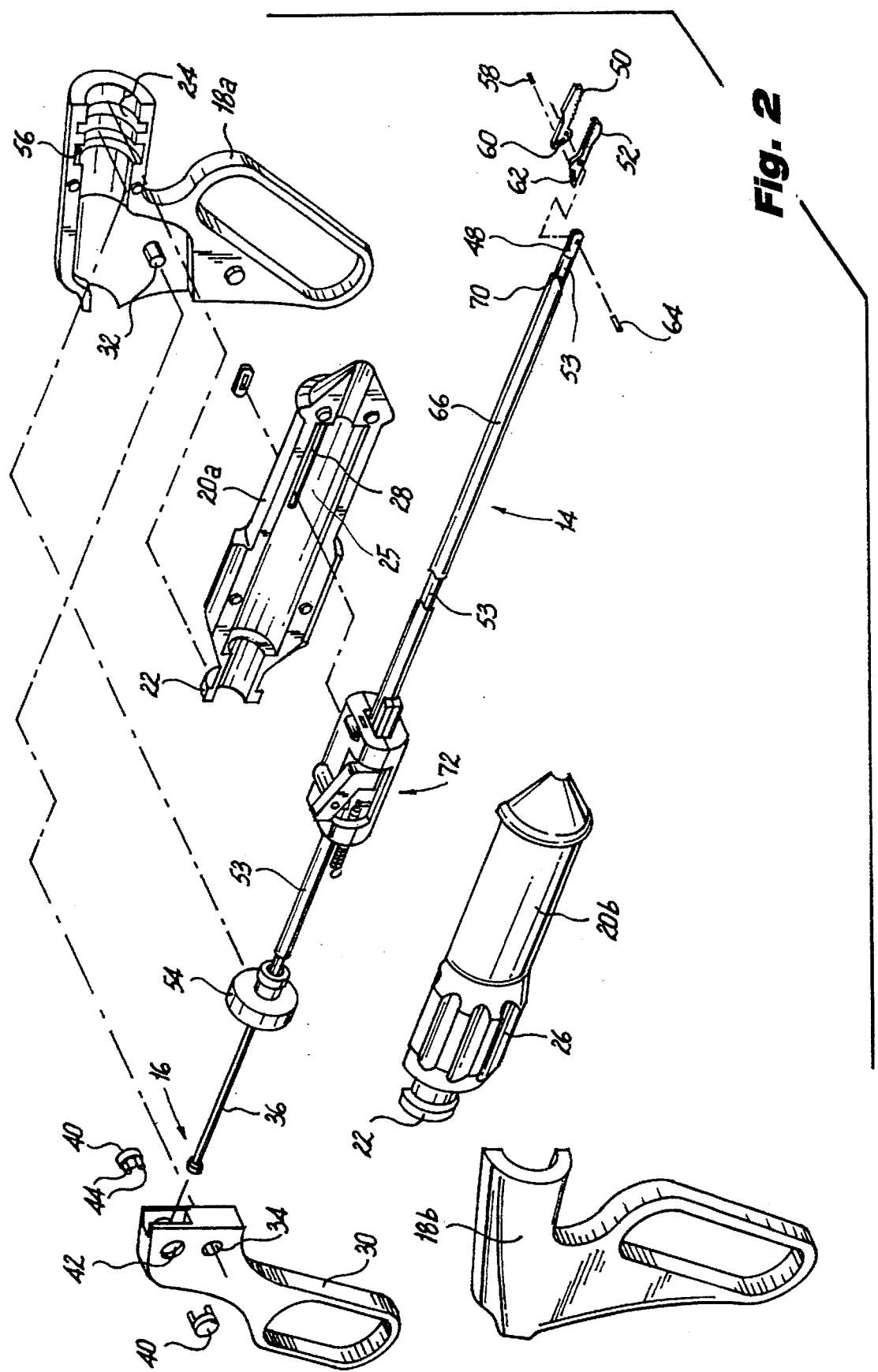
FIG. 2 is a perspective view with components separated of the surgical instrument of FIG. 1.

Referring to FIG. 2, frame 12 includes stationary handle 18 composed of left half 18a and right half 18b, and barrel section 20 composed of left half 20 and right half 20b. Barrel section 20 forms a head member 22 at its proximal end adapted for placement within groove 24 of stationary handle 18 to permit rotation of barrel section 20 with respect to stationary handle 18. Barrel section 20 defines a barrel chamber 25 adapted to contain a portion of tissue piercing assembly 14 and tool assembly 16. Barrel section 20 further includes a gripping portion 26 configured to be held by the operator to facilitate the rotation of barrel section 20. Longitudinal slot 28 is formed in barrel section 20 and is adapted to permit manipulation of tissue piercing assembly 14 by the operator.

Referring once again to FIG. 2, tool assembly 16 includes an actuation handle 30 pivotally connected to stationary handle 18 by pivot post 32 which extends from stationary handle left half 18a through pivot hole 34 in actuation handle 30. Control shaft 36 includes an engagement stem 38 at its proximal end, the engagement stem 38 attached to actuation handle 30 by fastener members 40. Fastener members 40 are positioned through fastener hole 42 in actuation handle 30 and include fastener fingers 44 which retain engagement stem 38 therebetween to secure control shaft 36 to actuation handle 30.

With continuing reference to FIG. 2, tool assembly 16 is associated with the distal end of control shaft 36. Tool assembly 16 includes a jaw housing 48, and a pair of cooperating jaw members 50 and 52 which are supported in jaw housing 48. Although the jaw members depicted herein are in the form of grasping jaws, it is envisioned that the jaw can take the form of biopsy forceps, cutting blades, needle holding jaws or dissecting jaws. Other jaw structures can also be employed. The construction and operation of tool assembly 16 is discussed in greater detail hereinbelow.

Referring once again to FIG. 2, control shaft 36 is slidably disposed through outer tube 53. Outer tube 53 is fixedly secured at a proximal end to bushing 54 and at a distal end to jaw housing 48. Bushing 54 is fixedly disposed within groove 56 in stationary handle 18 and is adapted to permit rotation of control shaft 36 within bushing 54.

Referring now to FIG. 1 in conjunction with FIG. 2, in operation, the jaw members 50 and 52 of tool assembly 16 are moved between an open position and a closed position through manipulation of actuation handle 30. As best seen in FIG. 1, pivotal movement of actuation handle 30 in the direction indicated by arrow "A" causes fastener members 40 to urge engagement stem 38 in a proximal direction. As a result, control shaft 36 is pulled in a proximal direction, drawing therewith a cam pin 58 which is associated with the distal end of control shaft 36 and jaw members 48 and 50. More specifically, as best seen in FIG. 2, cam pin 58 is dimensioned and configured to translate relative to a pair of angled cam slots 60 and 62 formed in jaw members 50 and 52 respectively. As cam pin 58 moves relative to cam slots 60 and 62, jaw members 50 and 52 move between open and closed positions as they pivot about a common pivot pin 64 which is supported in jaw housing 48.

Referring again to FIGS. 2–3, tissue piercing assembly 14 includes an elongated tubular member 66 having an axial bore 68 receiving control shaft 36 therethrough. Tubular member 66 defines a longitudinal axis and forms a tissue piercing portion 70 at its distal end. Control assembly 72 is disposed within barrel chamber 25 of barrel section 20 and is operatively associated with tubular member 66 of tissue piercing assembly 14 to control the longitudinal movement of tubular member 66 in relation to barrel section 20 of frame 12.

Figure 3:
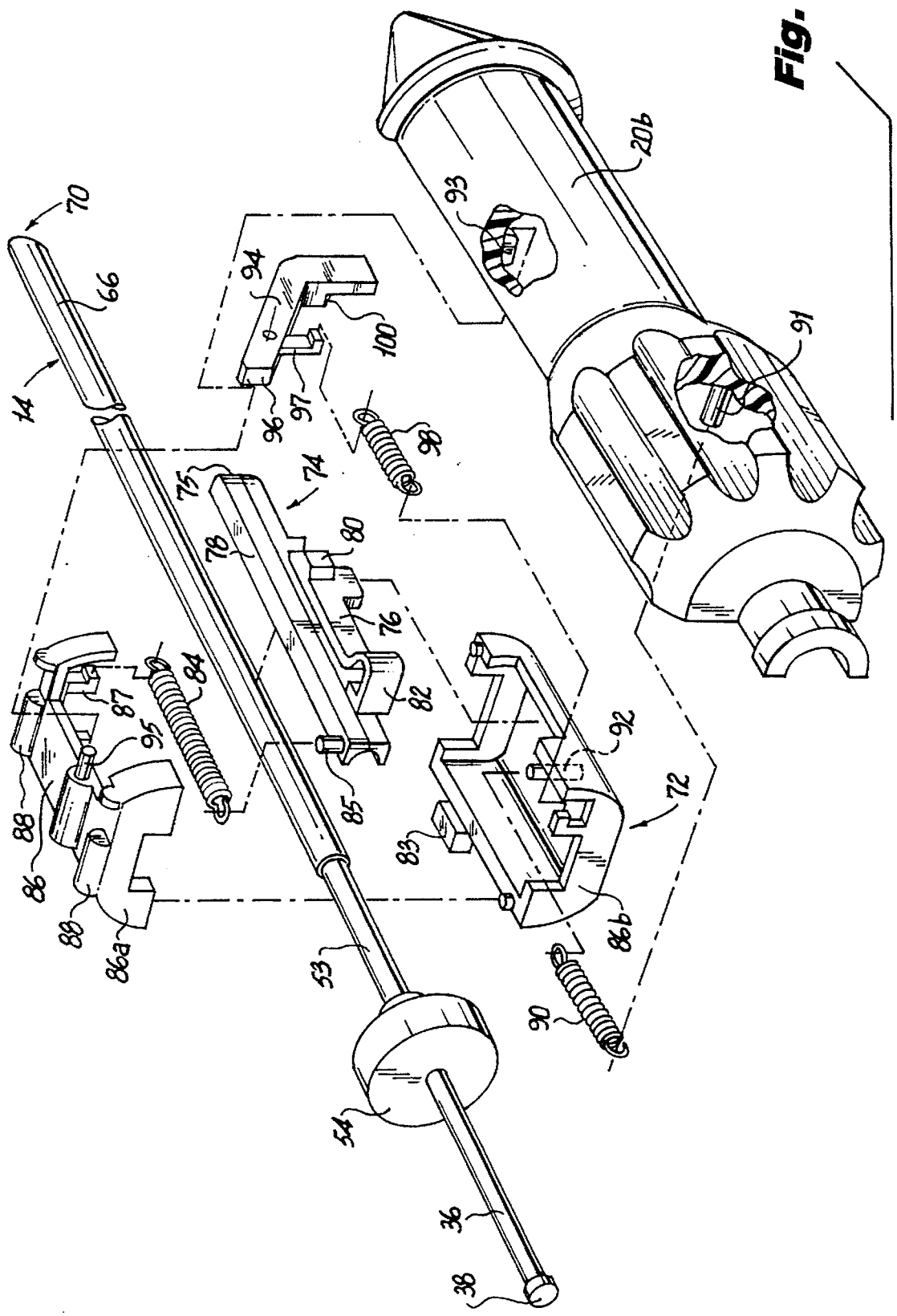
FIG. 3 is a perspective view with components separated of the control assembly of the surgical instrument of FIG. 1.

Referring to FIG. 3, control assembly 72 includes cam support member 74 mounted to tubular member 66 for conjoint axial motion. Flexible arm 76 extends from the body 78 of cam support member 74 and has an inclined cam face 80. Flexible arm 76 extends substantially parallel to body 78 of cam support member 74 and is deflectable relative to cam support member 74 through deflection in the "J-shaped" region 82 which joins the flexible arm 76 to the body 78 of the cam support member 74. Cocking spring 84 is anchored at a proximal end to cam support member 74 by post 85 and at a distal end to housing 86 by peg 87 and functions as described in detail hereinbelow.

With continuing reference to FIG. 3, the housing 86 is composed of top half 86a and bottom half 86b and is slidable within barrel section 20 of frame 12. Housing 86 includes a pair of outwardly directed spacers 88 formed on housing 86 which are adapted to maintain a clearance between housing and the inside wall (not shown) of barrel section 20. Return spring 90 is anchored at a proximal end to barrel section 20 by post 91 and at a distal end to housing 86 by post 92. An L-shaped catch 94 is pivotally mounted on post 95 of housing 86 and includes a latching face 96. Catch 94 further includes a downwardly extending catch arm 97 to which is mounted the distal end of a catch spring 98, the proximal end of catch spring 98 mounted to the housing 86. An angular camming face 89 is formed on catch 94 facing flexible arm 76 of cam support member 74. On the inside wall of barrel portion 20 is a ledge 93 against which latching face 96 of catch 94 engages when the instrument is "armed".

Referring now to FIG. 4, surgical instrument 10 is shown at a "rest" position with tool assembly 16 extending distally out from the distal end of tubular member 66. Referring to FIGS. 5–8, in operation the surgeon advances housing 86 distally relative to barrel section 20 by advancing distally a push button 83 (FIGS. 1 and 3) mounted to housing 86 and protruding through slot 28 in barrel section 20, thereby loading return spring 90. Housing 86 and cam support member 74 travel conjointly until such time as the front face 75 of the cam support member 74 contacts the distal wall 27 of barrel section 20 as shown in FIG. 5. At this point, further distal advancing of cam support member 74 is arrested, and further distal advancing of housing 86 causes cocking spring 84 to be loaded, that is, the housing 86 travels distally relative to the cam support member 74 thereby stretching cocking spring 84. As a result of this relative motion, the inclined cam face 80 on flexible arm 76 comes into contact with catch 94 as shown in FIG. 6.

Referring once again to FIG. 6, further distal movement of housing 86 and resultant contact between inclined cam face 80 of flexible arm 76 and catch 94 cause J-shaped region 82 to deflect as it comes into contact with catch 94. The relative positions and dimensions of the components are such that, when "fully armed" as shown in FIG. 7, the inclined cam face 80 is in contact with and deflected by the catch 94. If the surgeon released push button 83 at this point, the return spring 90 would cause immediate return of the housing 86 and the cam support member 74, to the rest position but for engagement between latching face 96 on catch 94 the ledge 93 on the inside wall of barrel section 20. The stroke of the housing 86 and cam support member 74 relative to barrel section 20 is such that tissue piercing portion 70 of tubular member 66 extends distally beyond tool assembly 16 when fully armed.

With reference to FIGS. 7–8, the surgeon now presses the tissue piercing portion 70 of tubular member 66 against the skin. The counterforce exerted by the skin causes tubular member 66, and therefore cam support member 74, to travel proximally, thereby further loading cocking spring 84 but, more importantly, placing the inclined cam face 80 of flexible arm 76 proximal of the angular camming face 89 of catch 94 where it assumes its non-deflected configuration in the plane of the catch 94. When the tissue piercing portion 70 of tubular member 66 pierces through the skin as shown in FIG. 8, the counterforce of the skin disappears, allowing the cocking spring to effect distal movement of the cam support member 74 relative to the housing 86. The inclined cam face 80 contacts the angular camming face 89 on the catch 94, causing counterclockwise pivotal motion of catch 94 against the bias of catch spring 98 removing latching face 96 out of engagement with ledge 93. Thus, the return spring 90 is unopposed and causes immediate retraction of the housing 86, and conjointly the cam support member 74, relative to barrel section 20. As a result, tissue piercing portion 70 of tubular member 66 is retracted proximal to tool assembly 16.

Referring now to FIG. 1 in conjunction with FIG. 8, with tool assembly 16 extending distal that of tissue piercing portion 70, tool assembly 16 can be manipulated by movement of actuation handle 30 to perform the surgical procedure.

In summary, the tissue piercing portion 70 of tubular member 66 immediately and automatically retracts upon entry through the skin placing the tool assembly 16 in position for use beyond the tissue piercing portion 70. Once exposed, the tool assembly 16 performs dual purposes, i.e., a safety function by protecting the tissue piercing portion 70 from contacting internal organs and a manipulation function by acting upon those same internal organs.

FIG. 9 illustrates an exemplary introducer 100 which may be used with a surgical instrument of the type shown in FIGS. 1–8. The introducer 100 includes a stabilizing structure 101 for stabilizing a surgical instrument at the surface of the body tissue adjacent where the surgical operation is to be performed. An accessing element 102 is coupled to the stabilizing structure 101 for establishing an opening through the body tissue surface layer and for providing a conduit for passage by a surgical instrument for accessing body tissue at the surgical site. The tissue piercing assembly 14 is used in conjunction with the stabilizing structure 101 and the accessing element 102 for puncturing through the body tissue surface layer.

As shown in FIGS. 9 and 10, stabilizing structure 101 includes a substantially circular skirt portion 106 and a longitudinally extending collar portion 108. Collar portion 108 defines a bore 199 extending proximally from the skirt portion 106 for receiving tissue piercing assembly 14 of surgical instrument 10. The skirt and the collar portions 106, 108 are preferably insert molded or over-molded to form a unitary assembly. Skirt portion 106 is preferably made of a flexible material such as polyurethane or polyethylene. A spring clamp 107 is preferably used to compress and secure an inserted surgical instrument within the stabilizing structure 101. The clamp 107 is preferably one which applies a tightening tension to a clamped object when no force is applied to the handles 198 of the clamp 107. The clamp 107 releases the clamped object when a force is applied at the handles 198. The collar portion 108 includes an annular notch 111 for seating clamp 107.

Figure 14:
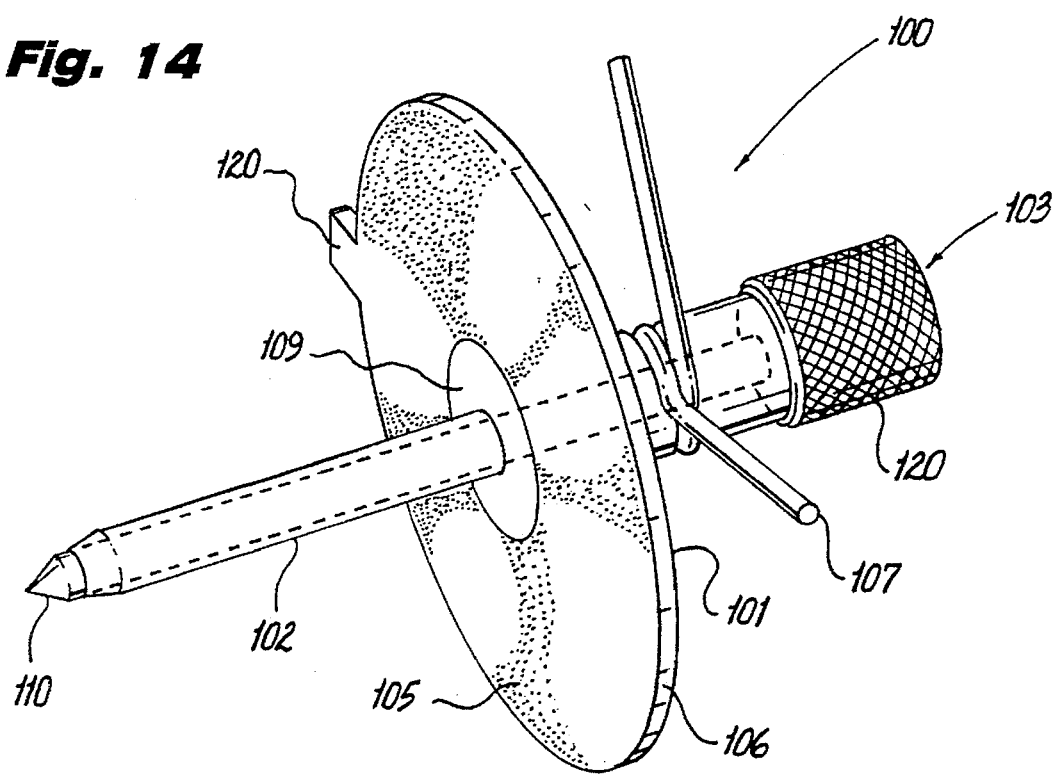
FIG. 14 is a perspective view of the introducer of FIG. 9 including an inserted obturator.
Figure 14A:
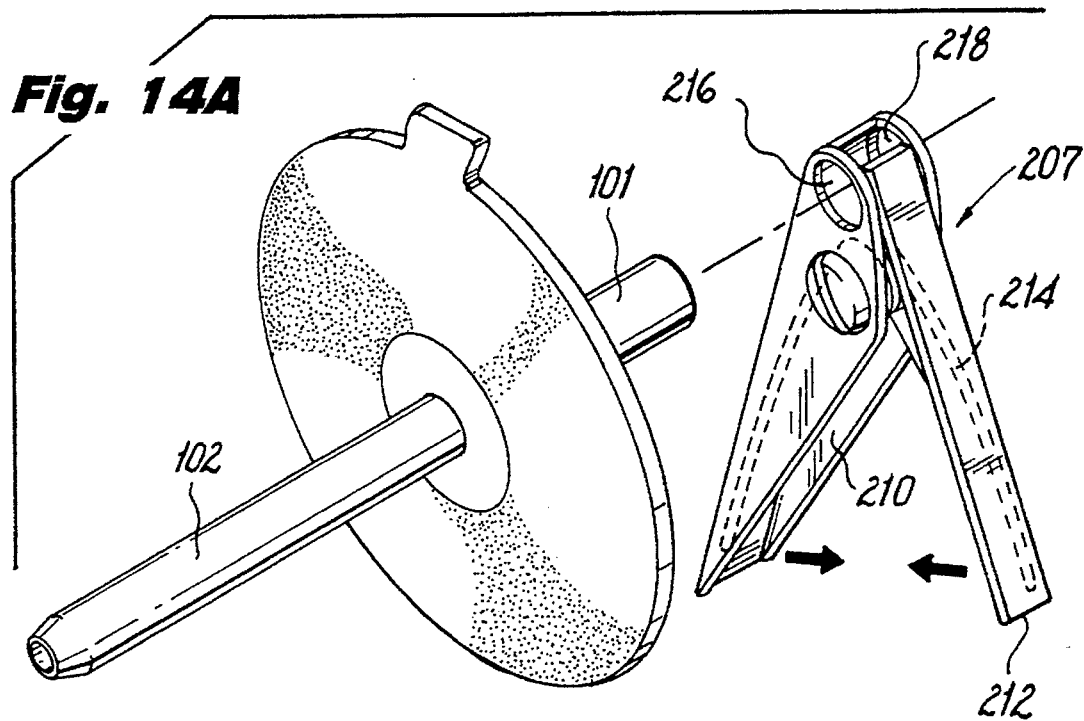
FIG. 14A is a perspective view of another clamping structure for applying a securing force to the stabilizing structure.
Figure 14B:
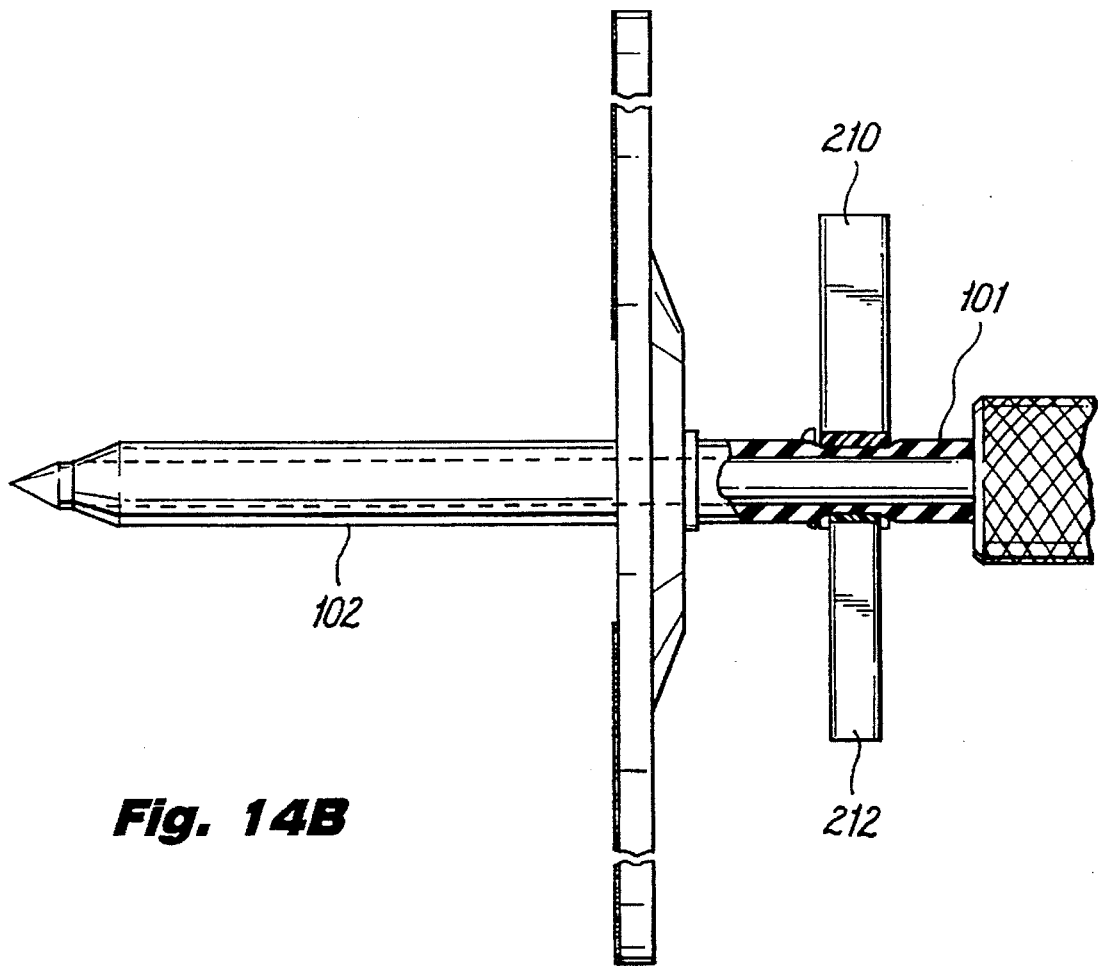
FIG. 14B is a side elevational view in partial cross-section of the stabilizing structure with the clamping structure of FIG. 14A secured thereon.
Figure 14C:
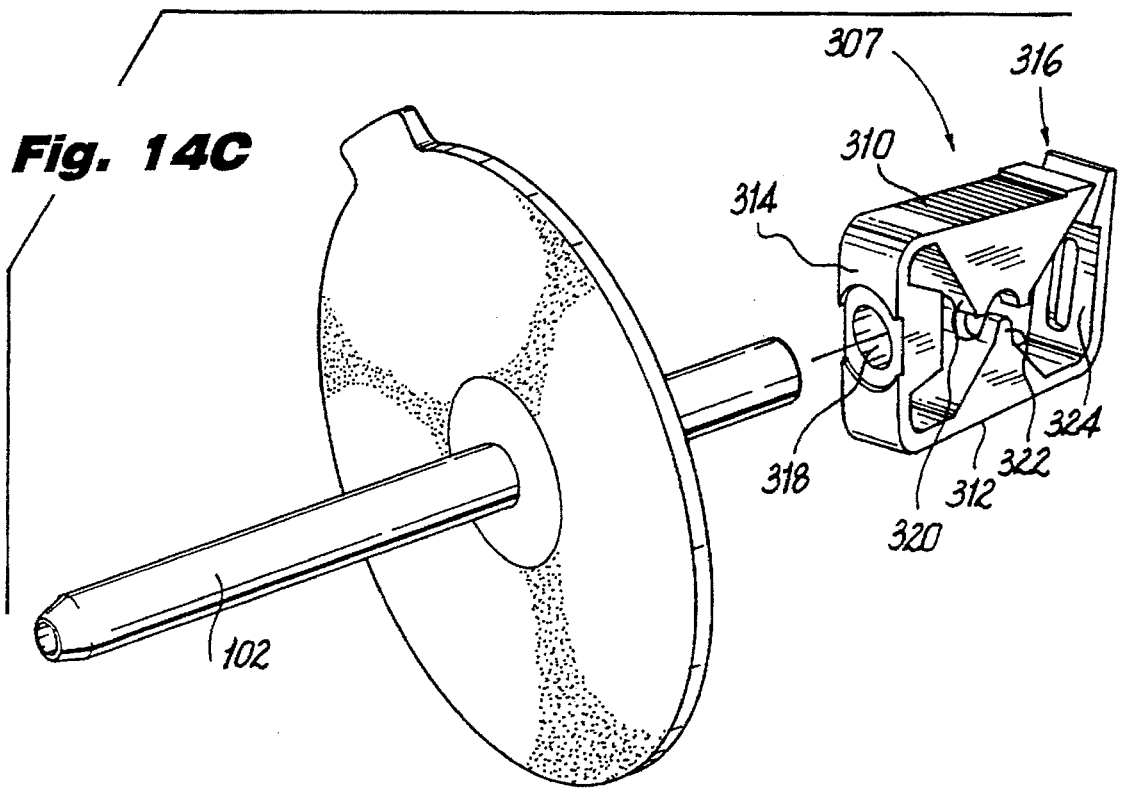
FIG. 14C is a perspective view of yet another clamping structure for applying a securing force to the stabilizing structure.

Alternative clamping structures 207 and 307 for applying a securing force to stabilizing structure 101 are illustrated in FIGS. 14A and 14C respectively. Referring to FIG. 14A, clamping structure 207 includes first and second pivotally connected clamp arms 210 and 212 which are normally biased into a clamping position by an internal torsion spring 214. An aperture 216 is defined at the distal end of clamp arm 210 for receiving stabilizing structure 101 and a clamp finger 218 is defined at the distal end of clamp arm 212 for engaging stabilizing structure 101 when clamping structure 207 is in the clamping position illustrated in FIG. 14B.

Figure 14D:
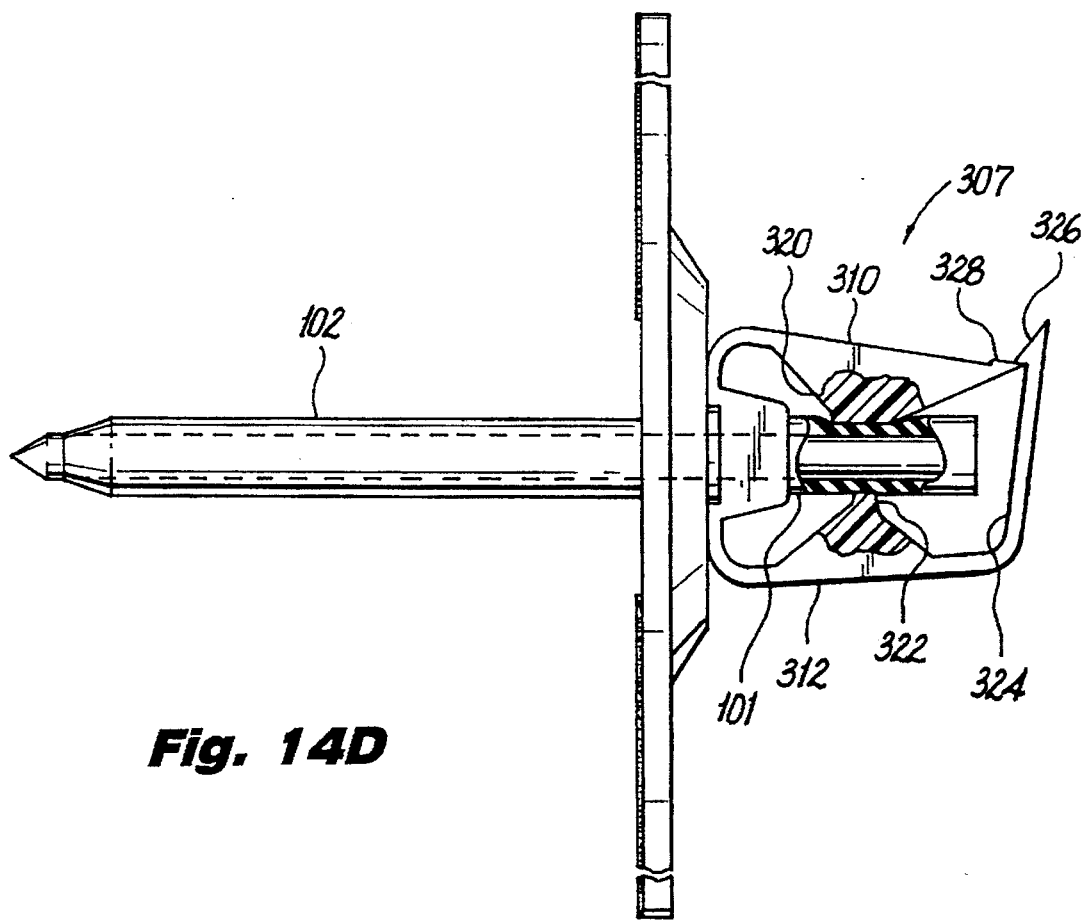
FIG. 14D is a side elevational view in partial cross-section of the stabilizing structure with the clamping structure of FIG. 14C secured thereon.

Referring to FIG. 14C, clamping structure 307 is of unitary construction and includes opposed clamping portions 310 and 312, a bridge portion 314 connecting the two clamping portions, and an integral locking assembly 316 formed opposite bridge portion 314. An aperture 318 is formed in bridge portion 314 for receiving stabilizing structure 101. A strut 320 depends inwardly from clamping portion 310 and a protuberance 322 depends inwardly from clamping portion 312 to engage stabilizing structure 101 at diametrically opposed locations on its periphery. Locking assembly 316 includes a spring leg 324 which depends from clamping portion 312. A tooth 326 is formed at the end of spring leg 324 for engaging a corresponding tooth 328 formed on clamping portion 310 to lock clamping structure 307 in the clamped position illustrated in FIG. 14D.

Referring again to FIGS. 9 and 10, the skirt portion 106 includes an adhesive layer 105 on the tissue engaging surface thereof. Preferably, the adhesive is a medically acceptable adhesive suitable for contacting body tissue surface or skin without medically adverse effects, e.g., a suitable rubber based adhesive. The adhesive layer 105 may be covered by release sheets 104A and 104B until ready for application to the body tissue surface. Release sheets 104a and 104b are semicircular in shape and sized to cover the entire adhesive layer of the skirt portion 106 for protecting the adhesive layer 105.

When the stabilizing structure 101 is ready for positioning at the body tissue surface adjacent to the surgical site, the release sheets 104a and 104b are removed by pulling on release tabs 104c and 104d to expose the adhesive layer 105. The stabilizing structure 101 is then ready for insertion and placement.

When removal of the stabilizing structure 101 from the body tissue surface is desired, skirt tab 120 is lifted and the skirt portion 106 is peeled away from the body tissue surface. The adhesive layer 105 of the skirt portion 106 is configured for releasably securing the stabilizing structure 101 and thereby the introducer 100 relative to the body tissue surface. The material of construction of the stabilizing structure 101 facilitates conformance of the skirt portion 106 to the contours of the body tissue surface, providing form fitting engagement and therefore strong adhesion of the skirt portion to the body tissue surface. It is understood that the skirt portion 106 is not limited to being circular, but may vary in shape, such as oval or rectangular.

Figure 13:
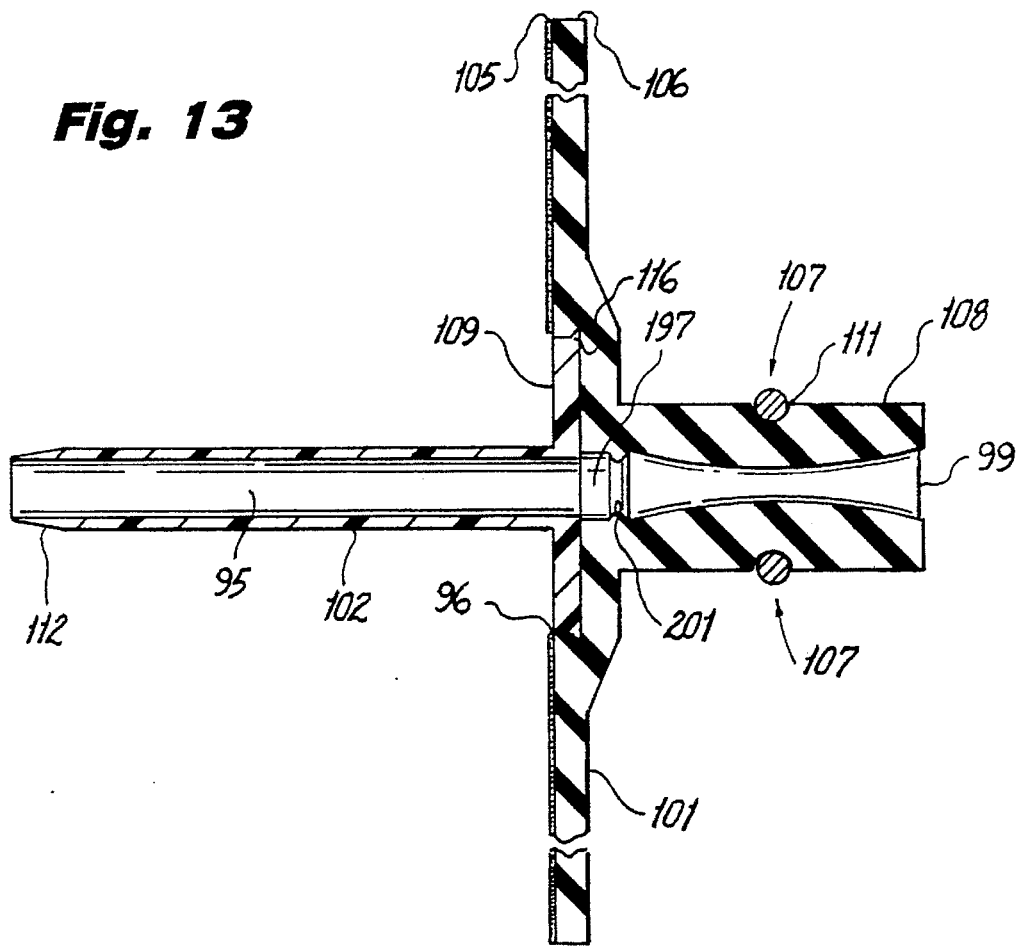
FIG. 13 is a cross-sectional side view of the stabilizing structure and the accessing element of the introducer of FIG. 9.

According to the embodiment of FIGS. 9 and 10, the skirt portion 106 is approximately two inches in diameter and has a thickness of approximately 0.05 inch at the outer circumferential portion thereof. Referring to FIG. 13, toward the center of the skirt portion 106, there is an upward elevation at a pitch of approximately 30°, and then leveling at approximately 0.25 inch from the center, forming a second circular opening or void 197 which is also concentric to the bores 199 of the stabilizing structure 101 and the first opening 196 of the skirt portion. The second opening 196 is in the same shape and size as shown for circular flange 109 of accessing element 102.

The collar portion 108 extends proximally and longitudinally from the skirt portion 106. The collar portion 108 is preferably circular and has an outer diameter of approximately 0.28 inch and a bore 199 having a diameter constricted for facilitating the passage of a surgical instrument therethrough. As can be seen in FIG. 13, a seal 201 extends radially into the bore for frictionally engaging the outer surface of an inserted surgical instrument to form a seal.

Again referring to FIGS. 9, 10 and 13, an accessing element 102 includes a longitudinal bore 195 extending distally from the stabilizing structure 101. A circular flange 109 is disposed at the proximal end thereof for coupling to the skirt portion 106 of the stabilizing structure 101. The accessing element 102 extends longitudinally from the circular flange 109 and further includes a tapered distal end portion 112 for accessing body tissue and expanding an opening in body tissue. The longitudinal bore 195 of the accessing element 102 preferably has an inner bore diameter which corresponds to the inner diameters of bores 199 and 197. When the accessing element 102 is coupled to the stabilizing structure 101, the longitudinal bore 195 of the accessing element 102 is in concentric alignment and communication with the longitudinal bore 197 of the stabilizing structure 101.

Referring to FIGS. 9–12, the introducer 100 is used with the tissue piercing assembly 14 for puncturing body tissue. The tissue piercing assembly 14 is slightly smaller in diameter than the longitudinal bore 197 of the stabilizing structure 101 and accessing unit 102 for passage therethrough.

Figure 11:
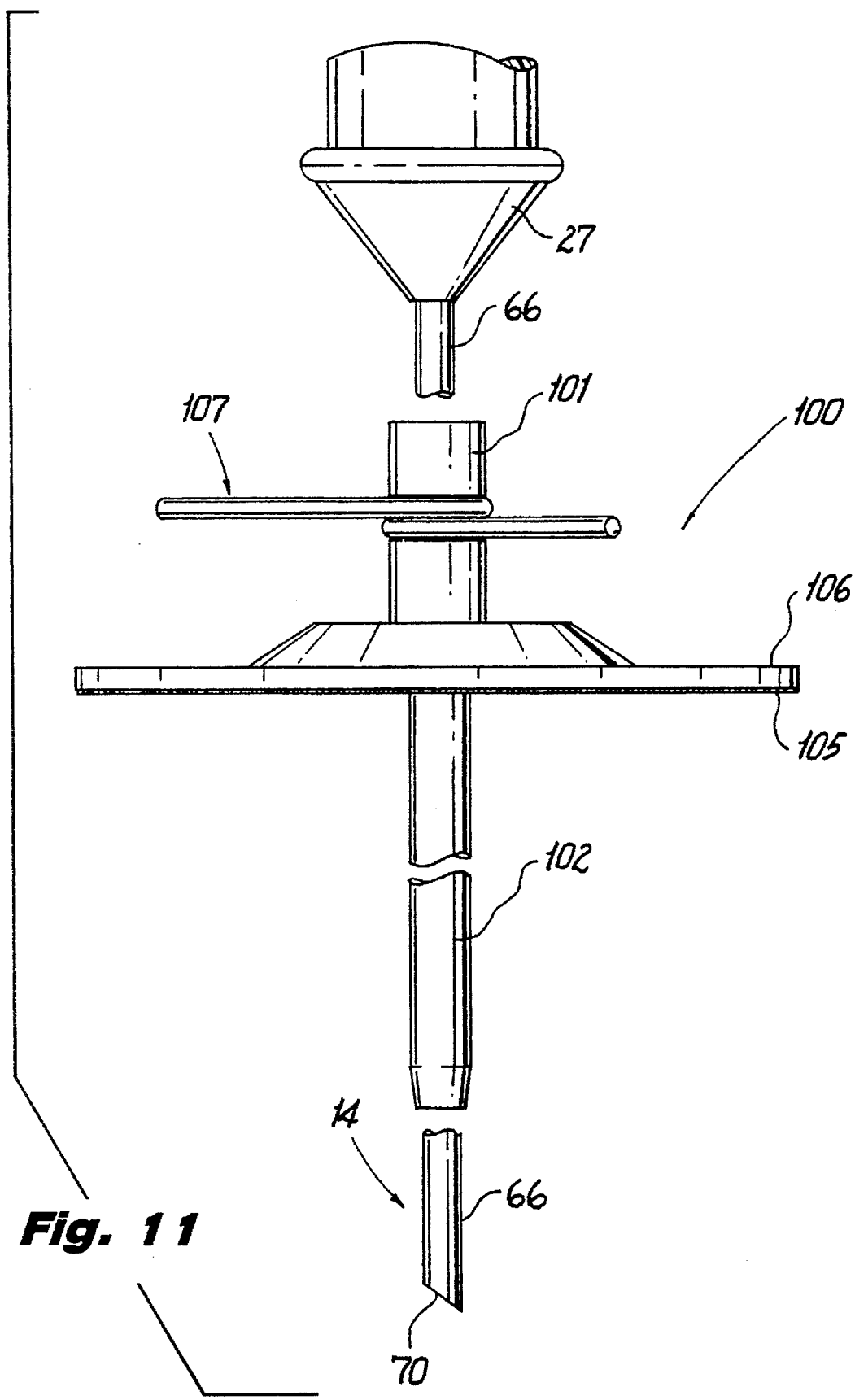
FIG. 11 is a front elevational view of the introducer of FIG. 10 including an inserted tissue piercing assembly.

Referring to FIG. 11, the accessing element 102 is coupled to the stabilizing structure 101 while tubular portion 66 of tool assembly 16 is inserted through the longitudinal bore of the stabilizing structure 101 and accessing element 102, until the tissue piercing portion 70 extends beyond the distal end portion of the accessing element 102. The tubular portion 66 is secured within the introducer 100 by clamp 107. The introducer 100, as shown in FIG. 11, is ready for application to the body tissue surface and for accessing the surgical site.

Figure 12:
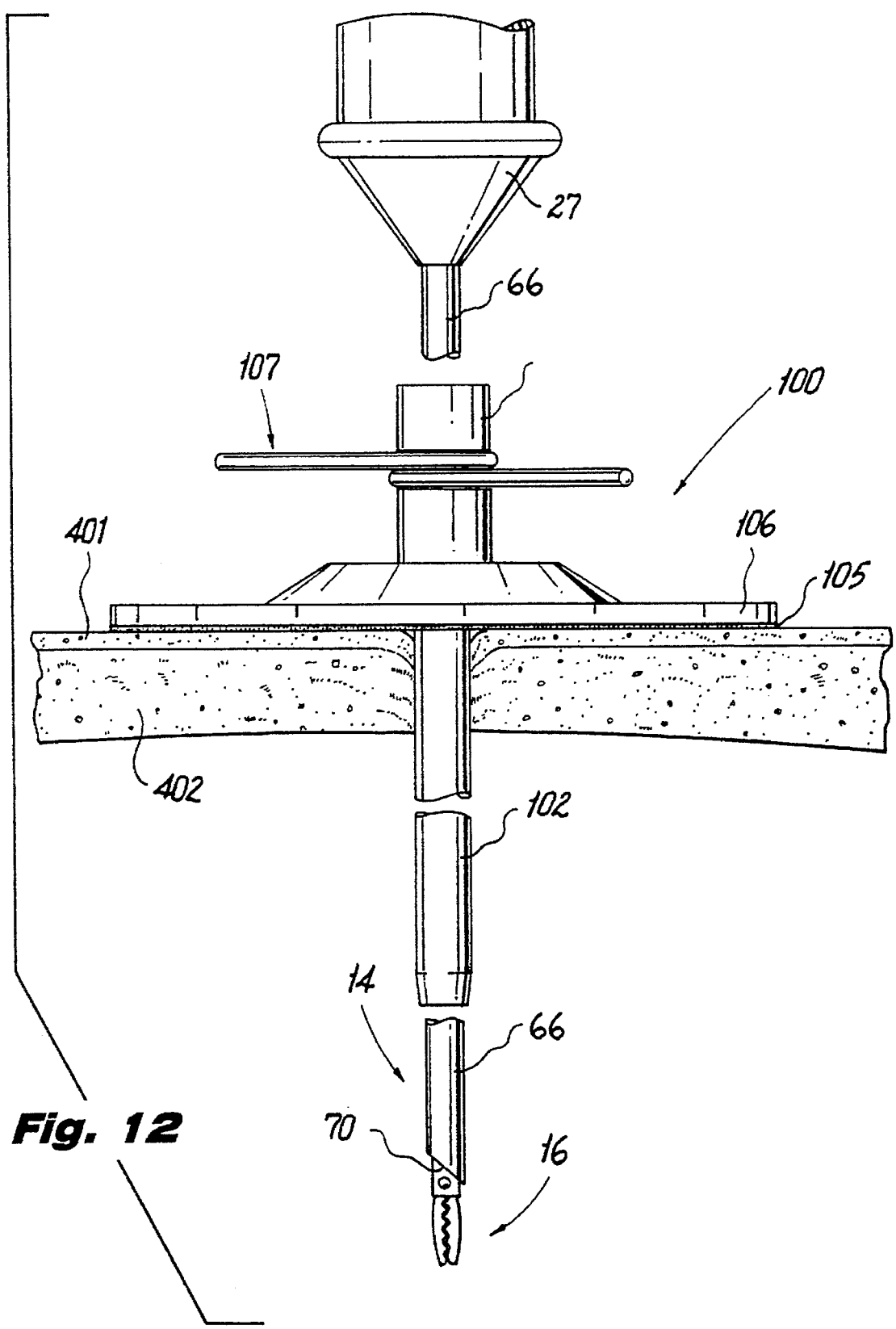
FIG. 12 is a front elevational view of the introducer of FIG. 10 after insertion through the body tissue.

FIG. 12 illustrates the introducer 100 having been positioned in the body tissue surface layer 402 subsequent the piercing of the body tissue surface layer 401 by tissue piercing assembly 14. Prior to insertion, release sheets 104a and 104b are removed to expose adhesive layer 105. Of course, the surgeon may choose to expose adhesive layer 105 after penetration is accomplished, if desired. The introducer 100 is affixed to body tissue surface 410 by adhesive layer 105. The flexible characteristics of the stabilizing structure 101 and skirt portion 106 allow conformity of the skirt portion 106 even if there are contours in the body tissue surface 410. This forms a strong bank to secure the introducer 100 to the body tissue surface 401. Tool assembly 16 can now be manipulated to perform the surgical procedure.

Figure 15:
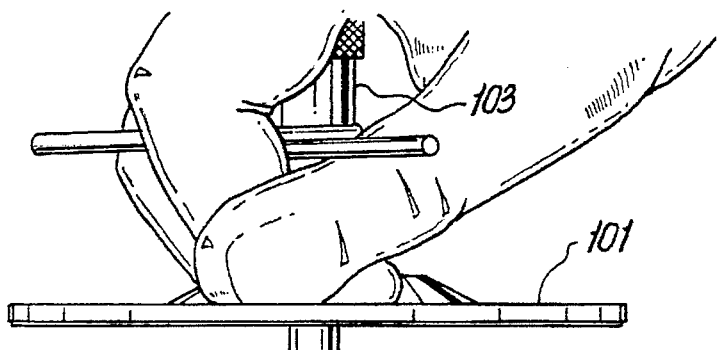
FIG. 15 is a view of the introducer of FIG. 14 being inserted through the body tissue.
Figure 16:
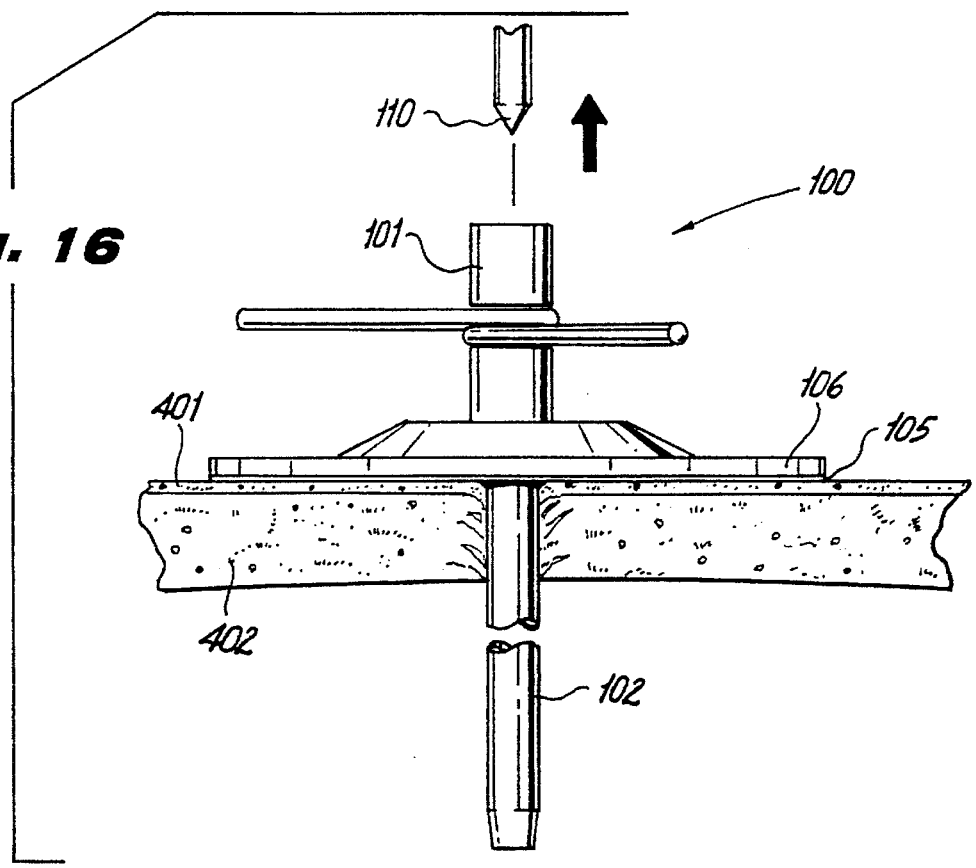
FIG. 16 is a view of the introducer of FIG. 14 after insertion through the body tissue, with the obturator removed.

However, as illustrated in FIGS. 14–16, the introducer 100 may also be used in conjunction with an obturator 103. The obturator 103 includes a sharp tip portion 110 at its distal end for puncturing body tissue. The outer surface of the proximal end portion 120 is diamond-knurled for providing non-slip engagement with the user. The operation of the introducer 100 with the obturator 103 is described in detail hereinbelow.

Referring again to FIG. 13, spring 107 is seated in its tension-applied position at annular notch 111. It can be seen that without a surgical instrument inserted in the stabilizing structure 101, the tension from spring 107 causes the flexible material of the stabilizing structure 101 to flex in an inward direction into the bore of the collar portion 108.

As shown in FIG. 14, the accessing element 102 is coupled to the stabilizing structure 101 while the obturator 103 is inserted through the longitudinal bore of the stabilizing structure 101 and accessing element 102, until the obturator tip 110 extends beyond the distal end portion of the accessing element 102. The obturator 103 is secured within the introducer 100 by clamp 107. The introducer 100, as shown in FIG. 14, is ready for application to the body tissue surface and accessing the surgical site.

FIG. 15 illustrates the introducer 100 being used to puncture the body tissue surface layer 401 by applying a vertically downward force into the body tissue surface. Prior to penetration, the release sheets 104a and 104b are removed to expose adhesive layer 105. Of course, as described above, the surgeon may choose to expose adhesive layer 105 after penetration is accomplished, if so desired.

Figure 17:
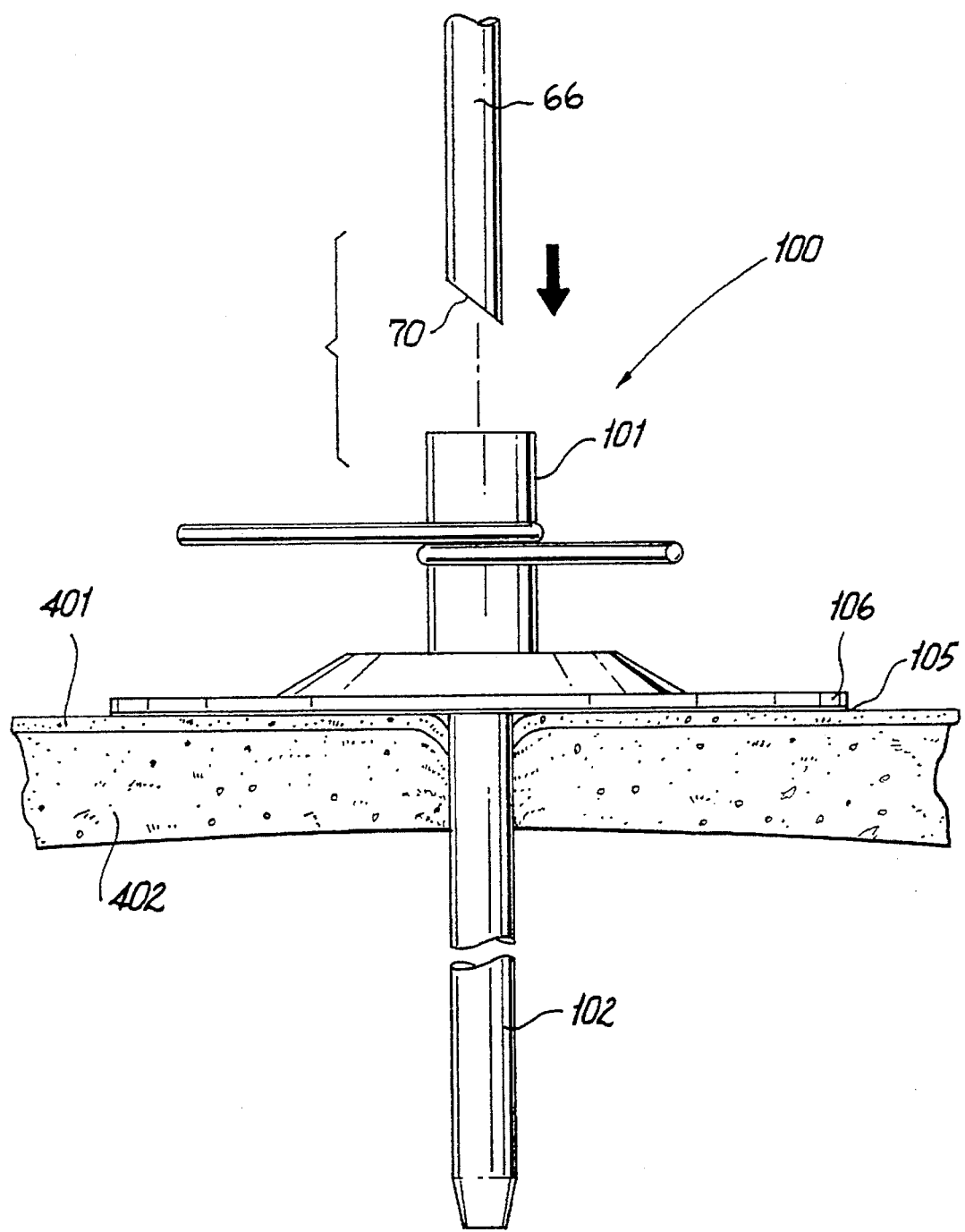
FIG. 17 is a view of the introducer of FIG. 15 after insertion through the body tissue, with the tissue piercing assembly being inserted through the accessing element.

FIG. 16 illustrates the introducer 100 after penetrating the body tissue surface layer 402 and with the obturator 103 removed. As shown, the introducer 100 is affixed to body tissue surface 401 by adhesive layer 105. Once again, the flexible characteristics of the stabilizing structure 101 and skirt portion 106 allow conformity of the skirt portion 106 even if there are contours in the body tissue surface 401. This forms a strong bond to secure the introducer 100 to the body tissue surface 401. The introducer 100 is now positioned to receive tubular member 66 of tissue piercing assembly 14 through the bore 199 of the stabilizing structure 101 and accessing element 102 as shown in FIG. 17. Accessing element 102 establishes an opening and isolates the tissues surrounding the accessing element 102 so that surgical instruments can be withdrawn or inserted through the longitudinal bore 99 without having to re-establish or find the opening each time a surgical instrument is replaced. Advantageously, the flexible characteristic of the stabilizing structure 101 and the flexible coupling arrangement of the accessing element 102 to the stabilizing structure 101 facilitate ample flexible movement of an inserted surgical instrument.

Upon completion of the surgical procedure, or if the introducer 100 needs to be released from the body tissue surface 401, tab 120, (FIG. 14) is lifted to release the adhesive layer 105 and the introducer 100 from the body tissue surface 401.

Figure 18:
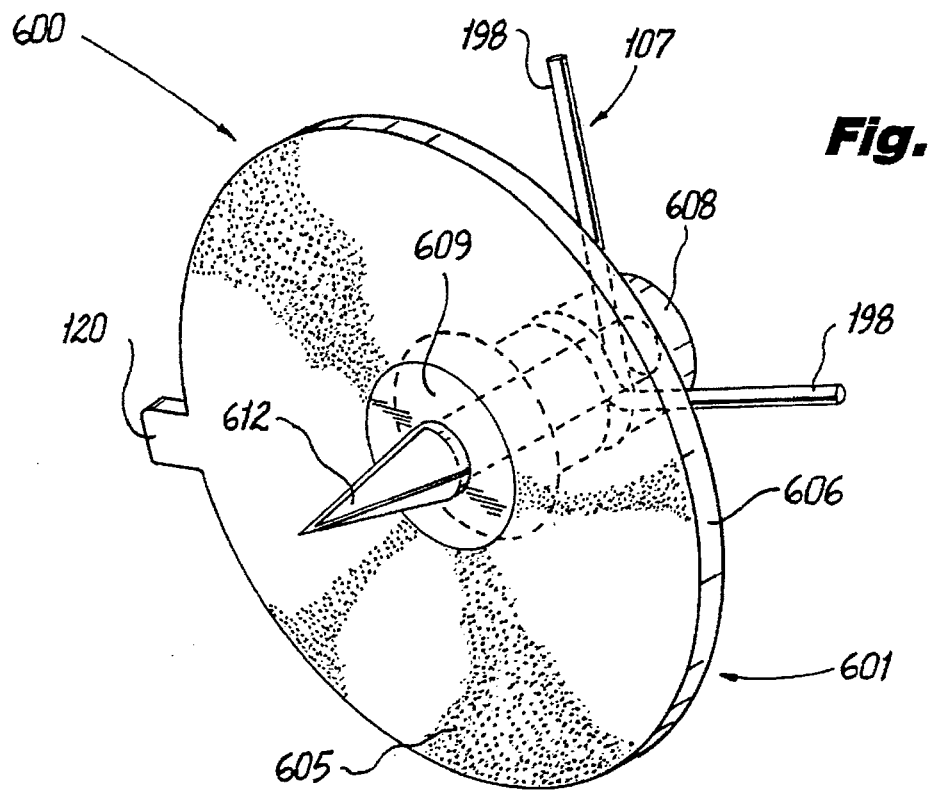
FIG. 18 is a distal to proximal perspective view of another preferred embodiment of the introducer of the present application.
Figure 19:
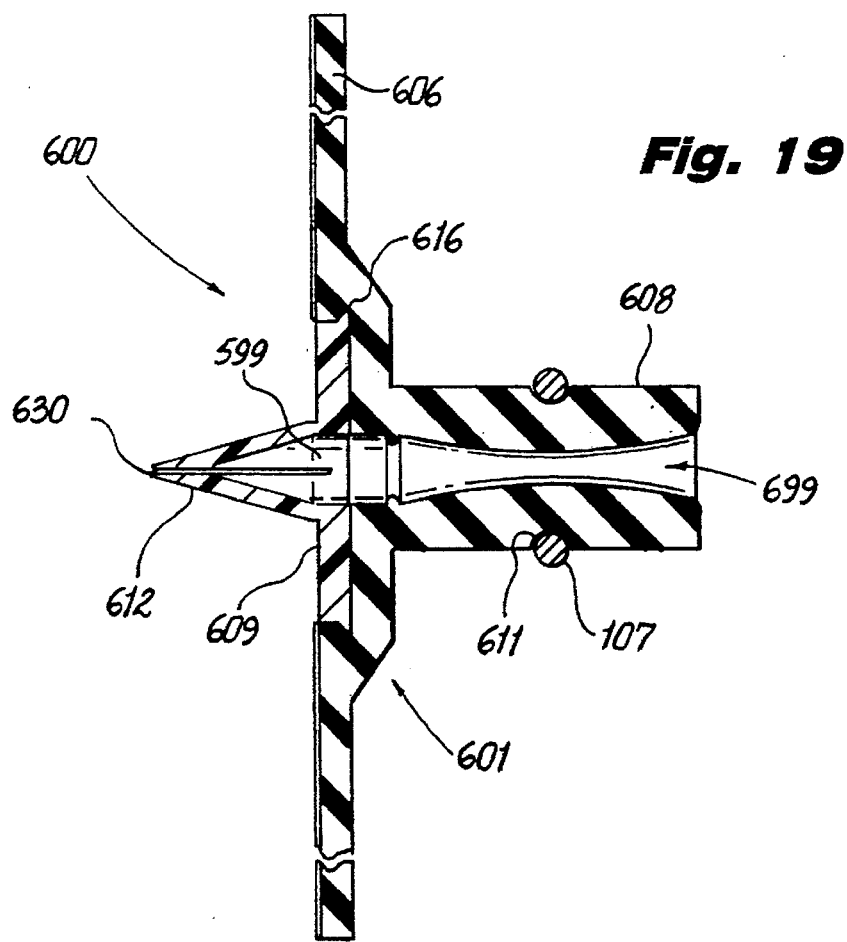
FIG. 19 is a side cross-sectional view of the embodiment of FIG. 18.

Referring now to FIGS. 18 and 19, an alternative introducer 600 is shown. The stabilizing structure 601 includes skirt portion 606 which is substantially the same in function as the skirt portion 106 of the embodiment of FIG. 9. The collar portion 608 includes a constricted bore 699, which has a smaller bore diameter opposite the annular notch 611 than the bore diameter adjacent the proximal end. This configuration facilitates the passage of a surgical instrument and the smaller bore diameter forms a seal against the inserted surgical instrument. Accessing element 602 comprises a circular flange 609 for coupling to the circular void 196 of the skirt portion 606 of the stabilizing structure 600, essentially as described above. The accessing element 602 further includes a conical stub 612, which extends longitudinally from the skirt portion 106. The conical stub 612 tapers distally to form a penetrating tip at the distal end for penetrating the body tissue surface. Such configuration eliminates the need for a separate obturator such as obturator 103 discussed above.

Referring to FIG. 19, the accessing element 602 preferably includes a bore 599 which is concentric to and in communication with the bore 699 of the stabilizing structure 601 when the accessing element 602 is coupled to the stabilizing structure 601. Slit openings 630 essentially divide the conical stub 612 into four equilateral portions, thereby facilitating the separation and the spreading apart of the conical stub 612 radially outwardly when a surgical instrument is inserted through the bore of the stabilizing structure 606 and the accessing element 602. (See FIG. 22) Accessing element 602 is preferably made from a semi-rigid material such as, for example, a biocompatible plastic.

Advantageously, the introducer 600 provides integral means for percutaneously accessing a surgical site beneath the body tissue surface while establishing a fixed point of entry of a surgical instrument, without any contact between the body tissue surface layer and the surgical instrument, regardless the number of times of entries, withdrawal, or replacements of surgical instruments through the introducer 600.

Figure 20:
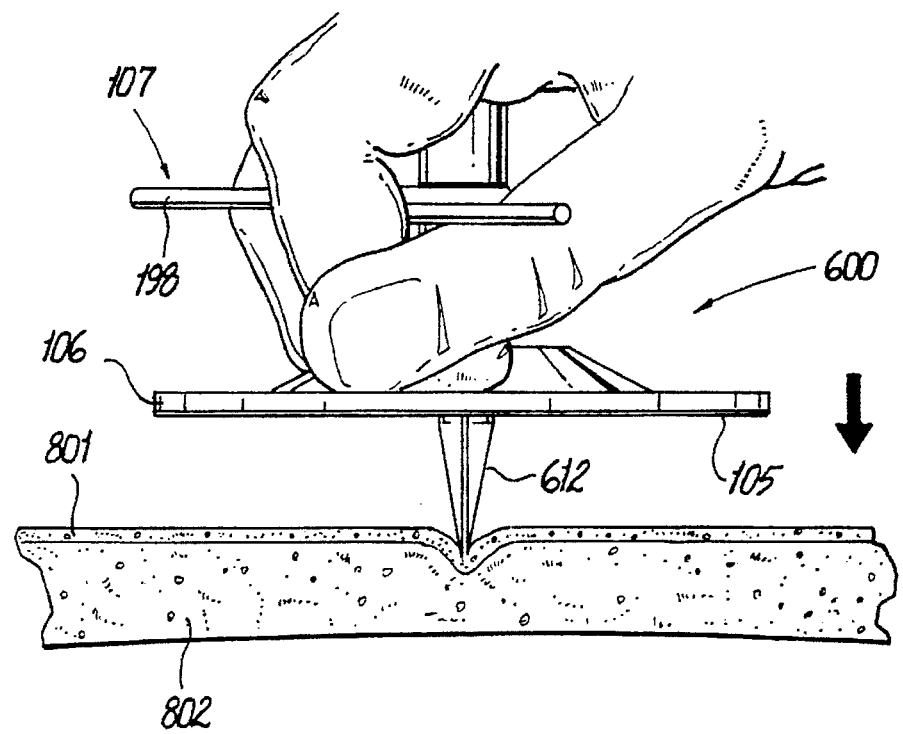
FIG. 20 is an elevational view of the introducer of FIG. 18 being inserted through the body tissue.
Figure 21:
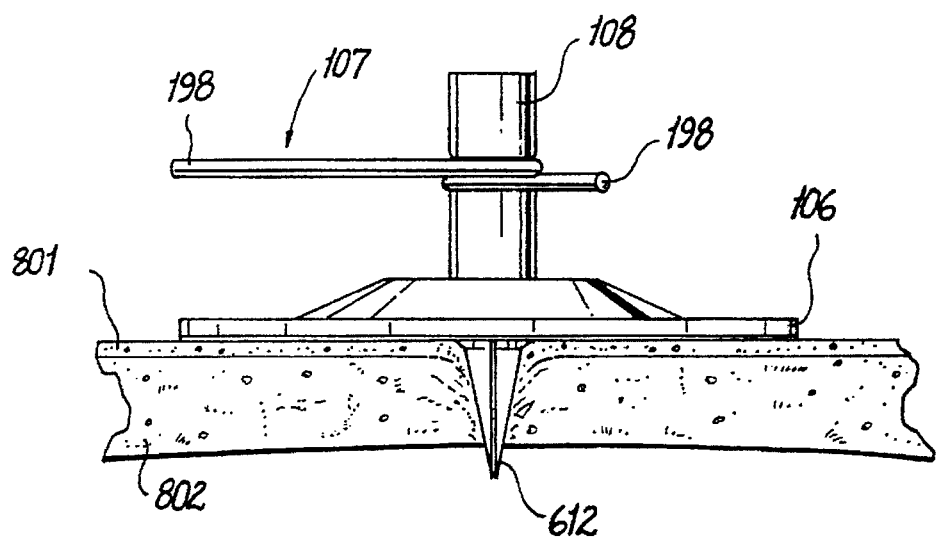
FIG. 21 is a view similar to FIG. 19 of the introducer of FIG. 18 being fully inserted into the body tissue.
Figure 22:
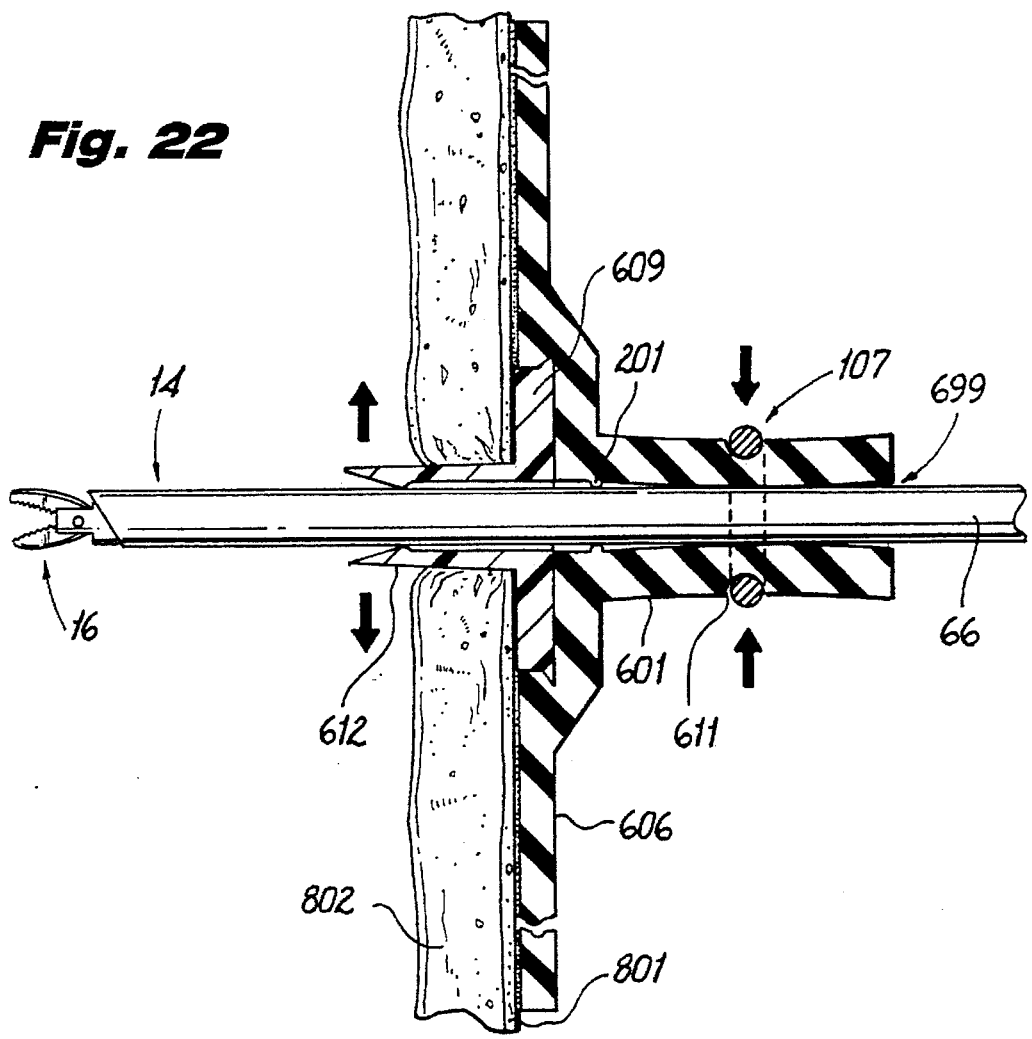
FIG. 22 is an elevational cross-sectional view of the introducer of FIG. 21 with the obturator removed, and with the tool assembly introduced therethrough.

FIGS. 20, 21 and 22 illustrate a preferred use of introducer 600. In FIG. 21, the penetrating tip of the conical stub 612 is used to create an opening in the body tissue surface 801 by a downward force on the introducer 600. The release sheets (not shown) have already been removed to expose the adhesive layer 105. FIG. 19 shows the introducer in place with the skirt portion 106 affixed to the body tissue surface 801 by the adhesive from the adhesive layer 105, thereby stabilizing the introducer 600. The conical stub 612 is shown to have cleared the body tissue surface layer 802 to expose the tip portion. If the thickness of body tissue surface layer is larger than the length of the conical stub 612, a cauterizing instrument may be inserted to contact the conical stub 612 to cauterize the contacting tissue.

FIG. 22 illustrates the introducer 600 with tubular member 66 of tissue piercing assembly 14 inserted therethrough and with tool assembly 16 in position to perform a surgical procedure. It can be seen that tubular member 66 has been inserted through the concentric bores of the collar portion 601 and skirt portion 606 of the stabilizing structure, and the circular flange 609 and the conical stub 612 of the accessing element 602. The conical stub 612 has radially parted from the slit against the tissue of the body tissue surface layer which surrounded the four portions. The clamp 107 clamps the tubular member 66 to the collar portion 101 and secures the tubular member 66 to the introducer 600. The tubular member 66 may be manipulated in a side-to-side or radial direction while secured to the introducer 600. It can be seen that the seal 201, which protrudes into the bore of the stabilizing structure, frictionally engages the tubular member 66 to form one seal and a second seal is formed by the engagement of the tubular member 66 with the smaller diameter portion of bore 699 opposite the annular notch 611. The surgical instrument 10 is shown, by way of an example, as a grasping instrument. It is understood that any surgical instrument, such as shears or a stapler, having a suitable shaft diameter for insertion through the introducer may be used.

Figure 23:
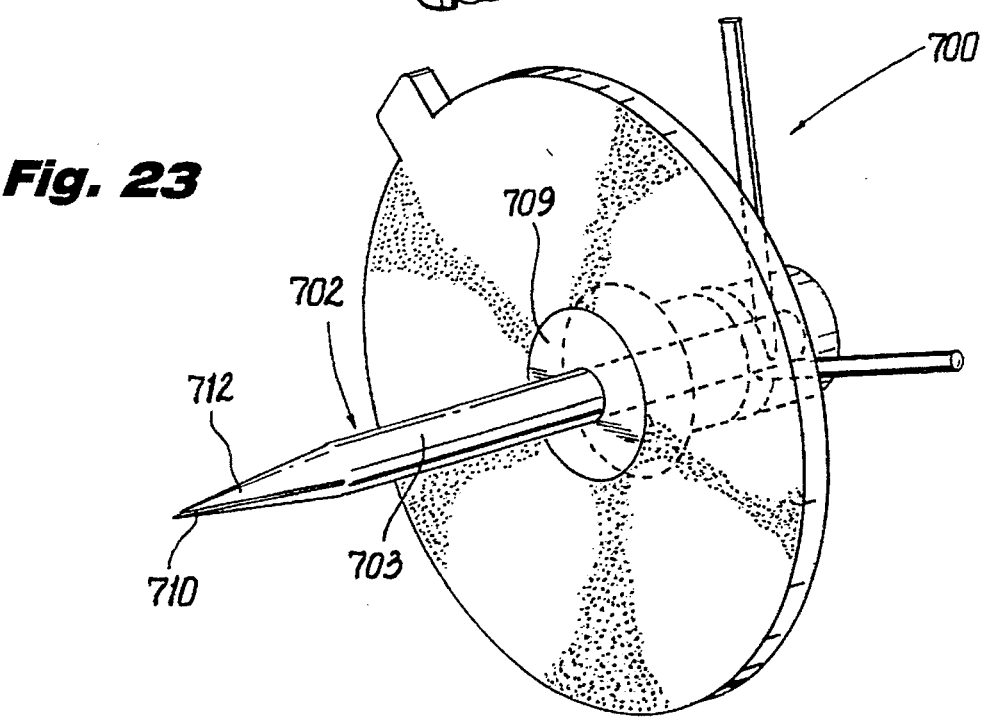
FIG. 23 is a distal to proximal perspective view of an introducer constructed in accordance with another preferred embodiment.

FIG. 23 illustrates another introducer embodiment. All aspects of the introducer 700 are the same as introducer 600 discussed above except that the accessing element 702 includes an elongated portion 703 between the circular flange 709 and the conical stub 712. The elongated portion 703 extends longitudinally to the conical stub 712 which tapers distally to form a penetrating tip 710.

In a preferred use, the introducer 700 is the same as described and shown in FIGS. 20-22. The length in the accessing element 702 is to accommodate surgical sites where the body tissue surface layer is thicker. In cases where the surgeon anticipates frequent insertion and reinsertion of surgical instruments through the introducer 700, which causes movement and disruption to the tissues of the body tissue surface layer surrounding the introducer 700, introducer 700 is preferred because the elongated portion of accessing element 702 ensures the clearance of the conical stub 712 from the body tissue surface layer.

It will be understood that various modifications can be made to the various embodiments herein disclosed without departing from the spirit and scope thereof. For example, various working members can be substituted for the graspers, dissectors, and surgical shears as appropriate for the particular procedure to be performed. In addition, for example, various sizes of the surgical instrument are contemplated, as well as various types of construction materials. Also, various modifications may be made in the configuration of the parts. For example, the skirt portion of the stabilizing structure may be rectangular rather than circular. The accessing element may be an integral unit of the stabilizing structure instead of a force fitting element. Therefore, the above description should not be construed as limiting the application but merely as exemplifications of preferred embodiments thereof. Those skilled in the art will envision other modifications within the scope and spirit of the present disclosure as defined by the claims appended hereto.

What is claimed is:

1. A surgical instrument for percutaneously accessing an operative site within a body, which comprises:

a frame having first and second ends;

a tissue piercing assembly having an elongated tubular portion forming a tissue piercing portion at a distal end, the elongated tubular portion defining a longitudinal axis;

a tool assembly disposed at least partially within the elongated tubular portion and having at least one working member; and an actuating mechanism operatively associated with the frame and the tool assembly, wherein the actuating mechanism manipulates the at least one working member.

2. The surgical instrument according to claim 1 further comprising a control assembly disposed adjacent the second end of the frame and operatively associated with the tissue piercing assembly, wherein the control assembly is adapted to control longitudinal movement of the tissue piercing assembly.

3. The surgical instrument according to claim 2, wherein the control assembly is configured to move the elongated tubular portion between a first position wherein the at least one working member is recessed within the elongated tubular portion, and a second position wherein the at least one working member extends distally out from the distal end of the tissue piercing assembly.

4. The surgical instrument according to claim 3, wherein the control assembly maintains the elongated tubular portion in the second position such that the tissue piercing portion of the elongated tubular portion may engage skin.

5. The surgical instrument according to claim 4, wherein the control assembly is further configured to automatically retract the elongated tubular portion to a retracted position proximal that of the at least one working member upon piercing of the skin by the tissue piercing portion.

6. The surgical instrument according to claim 5, wherein the elongated tubular portion is adapted to permit manipulation of the at least one working member when in the retracted position.

7. The surgical instrument according to claim 2, wherein the actuating mechanism comprises a movable handle pivotally connected at a first end to the frame, and at least one linking member having a first end operatively associated with the tool assembly and a second end operatively associated with the first end of the movable handle, wherein movement of the movable handle moves the at least one linking member to manipulate the at least one working member.

8. The surgical instrument according to claim 1, wherein the at least one working member is selected from the group consisting of a grasper, a dissector and a shearing element.

9. The surgical instrument according to claim 1 wherein the elongated tubular portion is a tube, and wherein the tissue piercing portion is the distal end of the tube.

10. The surgical instrument according to claim 9, wherein the distal end of the tube is beveled to form a cutting blade for piercing skin.

11. The surgical instrument according to claim 1 further comprising an introducer operatively associated with the tissue piercing assembly, the introducer adapted to facilitate the passage of the tissue piercing assembly in and out of the body.

12. A surgical instrument for percutaneously accessing an operative site within a body, which comprises:
  a frame having first and second ends;
  a tissue piercing assembly having an elongated tubular portion forming a tissue piercing portion at a distal end, the elongated tubular portion defining a longitudinal axis;
  a tool assembly disposed at least partially within the elongated tubular portion and having at least one working member;
  an actuating mechanism operatively associated with the frame and the tool assembly, wherein the actuating mechanism is adapted to manipulate the at least one working member; and
  a control assembly disposed adjacent the second end of the frame and operatively associated with the tissue piercing assembly, wherein the control assembly is adapted to control longitudinal movement of the tissue piercing assembly.

13. The surgical instrument according to claim 12 further comprising a rotating assembly disposed on the frame and operatively associated with the actuating assembly to rotate the at least one working member about the longitudinal axis.

14. The surgical instrument according to claim 13, wherein the second end of the frame forms a stationary handle, and wherein the actuating mechanism comprises a movable handle pivotally connected at a first end to the frame, and at least one linking member having a first end operatively associated with the tool assembly and a second end operatively associated with the first end of the movable handle, wherein movement of the movable handle moves the at least one linking member to manipulate the at least one working member.

15. The surgical instrument according to claim 14 wherein the at least one working member is a pair of graspers.

16. A surgical instrument for percutaneously accessing an operative site within a body, which comprises:
  a frame having first and second ends;
  a tissue piercing assembly having an elongated tubular portion forming a tissue piercing portion at a distal end, the elongated tubular portion defining a longitudinal axis;
  a tool assembly disposed at least partially within the elongated tubular portion and having at least one working member;
  an actuating mechanism operatively associated with the frame and the tool assembly, wherein the actuating mechanism is adapted to manipulate the at least one working member;
  a stabilizing structure defining a longitudinal axis and having a longitudinally extending bore therethrough adapted to receive a portion of the tissue piercing assembly and the tool assembly therethrough, a transversely oriented flexible tissue anchoring skirt positioned adjacent a distal end portion of the stabilizing structure, the skirt having an opening therein in communication with and concentric to the longitudinal bore of the stabilizing structure and a tissue engaging surface for releasably affixing the surgical instrument to a body tissue surface; and
  an accessing element extending distally from the flexible tissue anchoring skirt, the accessing element having a longitudinal bore therethrough, the accessing element longitudinal bore being in concentric alignment and communication with the skirt opening and the stabilizing structure bore, the accessing element having a tapered distal end portion for accessing body tissue.

17. A method of percutaneously accessing an operative site within a body, comprising the steps of:
  providing a surgical instrument including a tissue piercing assembly having an elongated tubular portion forming a tissue piercing portion at a distal end, at least one working member partially disposed within the elongated tubular portion, an actuating mechanism operatively associated with the at least one working member and adapted to manipulate the at least one working member, and a control assembly operatively associated with the tissue piercing assembly and adapted to control movement of the elongated tubular portion;
  engaging the skin of the body with the tissue piercing portion of the surgical instrument, the at least one working member disposed within the elongated tubular portion at a position proximal that of the tissue piercing portion;
  puncturing the skin with the tissue piercing portion, wherein the control assembly automatically retracts the elongated tubular portion to a position wherein the at least one working member extends out from the distal end of the elongated tubular portion in response to the puncturing of the skin; and
  manipulating the at least one working member below the skin.

18. The method according to claim 17, wherein the control assembly includes a spring assembly operatively associated with the elongated tubular portion and adapted to be loaded in response to a counterforce exerted on the tissue piercing portion of the elongated tubular portion by the skin, the spring assembly further adapted to move the tissue piercing portion to a position proximal that of the at least one working member upon piercing of the skin and subsequent removal of the counterforce on the tissue piercing portion.

19. A surgical instrument introducer for accessing body tissue, comprising:
  stabilizing structure defining a longitudinal axis and having a longitudinally extending bore therethrough adapted to receive a surgical instrument, a transversely oriented flexible tissue anchoring skirt positioned adjacent a distal end portion of the stabilizing structure, the skirt having an opening therein in communication with and concentric to the longitudinal bore of the stabilizing structure and a tissue engaging surface for releasably affixing the surgical instrument to a body tissue surface; and an accessing element extending distally from the flexible tissue anchoring skirt, the accessing element having a longitudinal bore therethrough, the accessing element longitudinal bore being in concentric alignment and communication with the skirt opening and the stabilizing structure bore, the accessing element having a tapered distal end portion for accessing body tissue.

20. The surgical instrument introducer according to claim 19, wherein the stabilizing structure is flexible.

21. The surgical instrument introducer according to claim 19, wherein the stabilizing structure includes a seal extending into the longitudinal bore, wherein the seal is adapted to frictionally engage a surgical instrument introduced therein.

22. The surgical instrument introducer according to claim 19, further including a clamp adapted to secure a surgical instrument against the longitudinally extending bore of the stabilizing structure.

23. The surgical instrument introducer according to claim 22, wherein the stabilizing structure includes an annular notch adapted to seat the clamp.

24. The surgical instrument introducer according to claim 19, wherein the tissue engaging surface of the flexible tissue anchoring skirt includes an adhesive layer configured to releasably affix the surgical instrument to a body tissue surface.

25. The surgical instrument introducer according to claim 24, wherein the flexible tissue anchoring skirt includes a tab configured to release the stabilizing structure from the body tissue surface.

26. The surgical instrument introducer according to claim 24, further including a removable non-adhesive layer adapted to substantially cover the adhesive layer when applied to the adhesive layer and further adapted to expose the adhesive layer when removed from the adhesive layer.

27. The surgical instrument introducer according to claim 19, wherein the accessing element is separately formed from the stabilizing structure and the stabilizing structure includes means for receiving the accessing element.

28. The surgical instrument introducer according to claim 27, wherein the accessing element includes a flange adjacent the proximal end portion for coupling to the stabilizing structure.

29. The surgical instrument introducer according to claim 19, further including an obturator for passing through the bores of the stabilizing structure and the accessing element, the obturator having a handle, a longitudinally extending elongated member, and a distally tapering tip for piercing through a body tissue surface.

30. The surgical instrument introducer according to claim 19, wherein the stabilizing structure is and the tissue anchoring skirt are insert molded.

31. The surgical instrument introducer according to claim 19, wherein the longitudinally extending bore of the stabilizing structure includes a restricted diameter portion for engaging a surgical instrument.

32. The surgical instrument introducer for accessing body tissue, comprising:

stabilizing structure having a collar defining a longitudinal axis and having a longitudinally extending bore therethrough for receiving a surgical instrument, a transversely oriented flexible tissue anchoring skirt positioned adjacent a distal end portion of the stabilizing structure, the skirt having an opening therein in communication with and concentric to the longitudinal bore of the collar and a tissue engaging surface for releasably affixing the surgical instrument to a body tissue surface; and an accessing element extending distally from the flexible tissue anchoring skirt, the accessing element having a longitudinal bore therethrough, the accessing element longitudinal bore being in concentric alignment and communication with the skirt opening and the collar bore, the accessing element having a tapered stub having a distal end tip for accessing body tissue.

33. The surgical instrument introducer according to claim 32, wherein the collar of the stabilizing structure is flexible.

34. The surgical instrument introducer according to claim 32, wherein the stub of the accessing element includes a slit for parting the stub, the stub being capable of extending radially outward when a surgical instrument is inserted through the accessing element.

35. The surgical instrument introducer according to claim 32, wherein the accessing element includes means for coupling to the stabilizing structure.

36. The surgical instrument introducer according to claim 35, wherein the means for coupling includes a flange for coupling to the stabilizing structure and an elongated longitudinal portion between the flange and the stub.

37. The surgical instrument introducer according to claim 32, wherein the collar and skirt are monolithically formed.

38. The surgical instrument introducer according to claim 32, wherein the longitudinally extending bore of the collar includes a restricted diameter portion for frictionally engaging a surgical instrument.

39. The surgical instrument introducer for accessing body tissue, comprising:

stabilizing structure defining a longitudinal axis and having a longitudinally extending bore therethrough for receiving a surgical instrument, a transversely oriented skirt portion positioned adjacent a distal end portion of the stabilizing structure, the skirt portion having a first opening therein in communication with and concentric to the longitudinal bore of the stabilizing structure, a flexible tissue engaging portion for releasably affixing the surgical instrument to a body tissue surface, and a second opening in the flexible tissue engaging portion being in communication with and concentric to the longitudinal bore and the first opening; and an accessing element extending distally from the flexible tissue anchoring skirt, the accessing element having a longitudinal bore therethrough, the accessing element longitudinal bore being in concentric alignment and communication with the first and second skirt openings and the stabilizing structure bore, the accessing element having a distally tapered distal end portion for accessing body tissue.

40. The surgical instrument introducer according to claim 39, wherein the accessing element includes a flange for coupling to the second opening of the flexible tissue engaging portion of the stabilizing structure.

41. The surgical instrument introducer according to claim 39, wherein the distally tapering distal end portion of the accessing element forms a tip portion for piercing through body tissue surface.

42. The surgical instrument introducer according to claim 39, wherein the tip portion includes a slit for separating the tip portion into substantially two half portions in a radially outward direction when a surgical instrument is introduced through the surgical instrument.

43. A method of percutaneously accessing an operative site within a body and for performing a surgical procedure within the body, comprising the steps of:

providing a surgical instrument including a tissue piercing assembly having an elongated tubular portion forming a tissue piercing portion at a distal end, at least one working member partially disposed within the elongated tubular portion, an actuating mechanism operatively associated with the at least one working member and adapted to manipulate the at least one working member, a control assembly operatively associated with the tissue piercing assembly and adapted to control movement of the elongated tubular portion, stabilizing structure having a bore extending therethrough adapted to receive at least a portion of the tissue piercing assembly therethrough and having a seal adapted to secure a surgical instrument introduced in the bore, a tissue anchoring skirt positioned adjacent the stabilizing structure having means for securing the skirt to a body tissue surface, the skirt having an opening therein in communication with the bore of the stabilizing structure and a tissue engaging surface, and an accessing element extending distally of the skirt the accessing element having a bore therethrough in communication with the bore of the stabilizing structure;

engaging a body tissue surface with the tissue piercing portion of the surgical instrument, the at least one working member disposed within the elongated tubular portion at a position proximal that of the tissue piercing portion;

puncturing the body tissue surface with the tissue piercing portion creating an access hole, wherein the control assembly automatically retracts the elongated tubular portion to a position wherein the at least one working member extends out from the distal end of the elongated tubular portion in response to the puncturing of the body tissue surface;

positioning the accessing element within the access hole;

securing the tissue engaging surface of the skirt to the body tissue surface with the means for securing;

securing the tissue piercing assembly to the stabilizing structure with the seal; and manipulating the at least one working member to perform the surgical procedure.

44. A method of percutaneously accessing an operative site within a body and for performing a surgical procedure within the body, comprising the steps of:

providing a surgical instrument including a tissue piercing assembly having an elongated tubular portion forming a tissue piercing portion at a distal end, at least one working member partially disposed within the elongated tubular portion, an actuating mechanism operatively associated with the at least one working member and adapted to manipulate the at least one working member, a control assembly operatively associated with the tissue piercing assembly and adapted to control movement of the elongated tubular portion, stabilizing structure having a bore extending therethrough adapted to receive at least a portion of the tissue piercing assembly therethrough and having a seal adapted to secure a surgical instrument introduced in the bore, a tissue anchoring skirt positioned adjacent the stabilizing structure having means for securing the skirt to a body tissue surface, the skirt having an opening therein in communication with the bore of the stabilizing structure and a tissue engaging surface, and an accessing element extending distally of the skirt the accessing element having a bore therethrough in communication with the bore of the stabilizing structure;

providing an obturator having a tissue piercing point;

engaging a body tissue surface with the tissue piercing tip of the obturator to create an initial access hole;

positioning the accessing element of the surgical instrument within the initial access hole;

securing the tissue engaging surface of the skirt to the body tissue surface with the means for securing;

inserting the tissue piercing portion of the surgical instrument into the initial access hole to engage a second body tissue surface;

puncturing the second body tissue surface with the tissue piercing portion creating an enlarged access hole, wherein the control assembly automatically retracts the elongated tubular portion to a position wherein the at least one working member extends out from the distal end of the elongated tubular portion in response to the puncturing of the second body tissue surface;

securing the tissue piercing assembly to the stabilizing structure with the seal; and manipulating the at least one working member to perform the surgical procedure.

* * * * *